US012618038B2

(12) United States Patent
Jones et al.

(10) Patent No.: US 12,618,038 B2
(45) Date of Patent: May 5, 2026

(54) DEVICE AND METHOD FOR MEASURING IN-CELL PROTEIN FOLDING

(71) Applicants: UNIVERSITY OF MARYLAND, BALTIMORE, Baltimore, MD (US); THE UNIVERSITY OF MASSACHUSETTS, Boston, MA (US)

(72) Inventors: Lisa Jones, Baltimore, MD (US); Anne Gershenson, Northampton, MA (US); Dante T. Johnson, Baltimore, MD (US)

(73) Assignees: UNIVERSITY OF MARYLAND, BALTIMORE, Baltimore, MD (US); THE UNIVERSITY OF MASSACHUSETTS, Boston, MA (US)

( * ) Notice: Subject to any disclaimer, the term of this patent is extended or adjusted under 35 U.S.C. 154(b) by 1185 days.

(21) Appl. No.: 17/042,565

(22) PCT Filed: Mar. 28, 2019

(86) PCT No.: PCT/US2019/024691
§ 371 (c)(1),
(2) Date: Sep. 28, 2020

(87) PCT Pub. No.: WO2019/191499
PCT Pub. Date: Oct. 3, 2019

(65) Prior Publication Data
US 2021/0062135 A1 Mar. 4, 2021

Related U.S. Application Data

(60) Provisional application No. 62/649,132, filed on Mar. 28, 2018.

(51) Int. Cl.
*C12M 1/00* (2006.01)
*C12M 1/34* (2006.01)
(Continued)

(52) U.S. Cl.
CPC ............ *C12M 41/14* (2013.01); *C12M 29/10* (2013.01); *C12M 41/46* (2013.01); *C12N 5/0068* (2013.01);
(Continued)

(58) Field of Classification Search
CPC ...... C12M 41/14; C12M 29/10; C12M 41/46; C12M 41/12; C12N 5/0068; C12N 2529/10; C12N 2521/00; G01N 33/6848
See application file for complete search history.

(56) References Cited

U.S. PATENT DOCUMENTS 3,929,584 A 12/1975 Mansfield
7,830,598 B2 * 11/2010 Tsuchiya ................ B01L 9/523
359/395
(Continued)

FOREIGN PATENT DOCUMENTS

WO WO-2008118500 A1 * 10/2008 ............ C12M 23/12
WO WO2016/145290 A1 9/2016
WO WO2016/164244 A1 10/2016

OTHER PUBLICATIONS

Ebbinghaus, et al., Protein folding stability and dynamics imaged in a living cell, Nat. Methods vol. 7, 2010, pp. 319-323.
(Continued)

*Primary Examiner* — Liban M Hassan
(74) *Attorney, Agent, or Firm* — Wolter Van Dyke Davis, PLLC; Eugene J. Molinelli; Cian G. O'Brien

(57) ABSTRACT

An apparatus, system, and method for studying protein folding in the native cellular environment is provided. The invention, termed pcIC-FPOP, combines pulse-chase experiments with in-cell protein footprinting coupled to mass spectrometry. This enables very high resolution information on the folding or mis-folding of proteins. The system (100) includes a multi-well plate (110), an incubator (120), a stage (130), a subsystem of reservoirs (172) and pumps (174), a
(Continued)

laser source (140) and beam steering optics (150), and a computer system (160) programmed with a control module (162) to control the operation of the laser (140), optics (150), incubator (120), stage (130), or pumps (174), or some combination. This method permits studies that fill gaps in knowledge on protein folding and its role in disease.

11 Claims, 22 Drawing Sheets

(51) Int. Cl.
C12N 5/00 (2006.01)
G01N 5/00 (2006.01)
G01N 33/68 (2006.01)
(52) U.S. Cl.
CPC ..... G01N 33/6848 (2013.01); C12N 2529/10 (2013.01)

(56) References Cited

U.S. PATENT DOCUMENTS

| | | | | |
|---|---|---|---|---|
| 8,501,115 B2 * | 8/2013 | Adey | ........................ | B01L 7/52 |
| | | | | 422/68.1 |
| 2002/0068358 A1 * | 6/2002 | Campbell | ............ | A01K 45/007 |
| | | | | 435/289.1 |
| 2006/0019926 A1 | 1/2006 | Paape | | |
| 2007/0217964 A1 * | 9/2007 | Johnson | ................. | C12M 41/00 |
| | | | | 422/130 |
| 2016/0369222 A1 * | 12/2016 | Cho | ....................... | C12M 23/12 |
| 2017/0058246 A1 * | 3/2017 | Grier, Jr. | ................ | C12M 41/34 |
| 2018/0105784 A1 * | 4/2018 | Asai | ........................ | C12M 41/48 |

OTHER PUBLICATIONS

Fenn et al., Electrospray Ionization for Mass Spectrometry of Large Biomolecules, Science vol. 246, 1989, pp. 64-71.

Gau, et al., Fast Photochemical Oxidation of Proteins Footprints Faster than Protein Unfolding, ANal Chem. 81 (16), 2009, pp. 6563-6571.

Hambly, et al., Laser Flash Photolysis of Hydrogen Peroxide to Oxidize Protein Solvent-Accessible Residues on the Microsecond Timescale, J. Am. Soc. Mass Spectrom., 2005, 16, pp. 2057-2063.

Hambly, et al., Laser flash photochemical oxidation to locate heme binding and conformational changes in myoglobin, Int. J. Mass Spectrom., 259, 2007, pp. 124-129.

Karas et al., Influence of the Wavelength in High-Irradiance Ultraviolet Laser Desorption Mass Spectrometry of Organic Molecules, Anal. Chem 57, 1985, pp. 2935-2939.

Nissley, et al., Accurate prediction of cellular co-translational folding indicates proteins can switch from post- to co-translational folding, Nat. Commun. 7, 2016.

Rinas, et al., An efficient quantitation strategy for hydroxyl radical-mediated protein footprinting using Proteome Discoverer, Anal. Bioanal. Chem. 408, 2016, pp. 3021-3031.

Rinas et al., Development of a Microflow System for In-Cell Footprinting Coupled with Mass Spectrometry, Anal. Chem. 88(20), 2016, pp. 10052-10058.

Smith, et al., NMR studies of protein folding and binding in cells and cell-like environments, Curr. Opin. Struct. Biol. 30, 2015, pp. 7-16.

Zhang et al., Protein Analysis by Shotgun/Button-up Proteomics, Chem. Rev. 113, 2013, pp. 2343-2394.

International Search Report and Written Opinion for International Patent Application No. PCT/US2019/024691 dated Jun. 13, 2019, pp. 1-11.

Espino et a l. "In Cell Footprinting Coupled with Mass Spectrometry for the Structural Analysis of Proteins in Live Cells," Analytical Chemistry, Jul. 6, 2015 (Jul. 6, 2015}, vol. 87, Iss. 15, pp. 7971-7978.

Johnson et.al "Innovation of a Novel Pulse-Chase in Cell Footprinting Method for the Study of Protein Folding Phenomena," Biophysical Journal, Feb. 15, 2019 (Feb. 15, 2019), vol. 116, Iss. 3, Suppl. 1, p. 339a.

Jones et al. "1 R0-1 GM128985-01: Development of a Novel Pulse-Chase in-Cell Footprinting Method for Protein Folding Analysis," NJH RePORTER, Jul. 24, 2018 (Jul. 24, 2018), pp. 1 of 1.

* cited by examiner 01.22.2019

FROM FIG. 12C-1

DEVICE AND METHOD FOR MEASURING IN-CELL PROTEIN FOLDING

CROSS-REFERENCE TO RELATED APPLICATIONS

This application is a 371 national stage application of PCT Application No. PCT/US19/24691, filed Mar. 28, 2019, and claims benefit of Provisional Application No. 62/649,132, filed Mar. 28, 2018, the entire contents of which are hereby incorporated by reference as if fully set forth herein, under 35 U.S.C. § 119 (e).

BACKGROUND

1. Field of the Invention

The invention pertains to an apparatus and method for studying protein folding in the native cellular environment. The apparatus and method combine pulse-chase experiments with in-cell protein footprinting coupled to mass spectrometry. An embodiment of the apparatus includes multiple fluid conduits for application of fluids to different wells of a multi-well plate inside an incubator to accomplish the pulse-chase treatment of cells expressing a protein of interest. The method can be used to determine the intracellular folding pathways of proteins, including mis-folding pathways that lead to disease.

2. Background of the Invention

Protein footprinting is a method that monitors protein conformation by selectively labeling/modifying or cleaving residues, where the selectivity is, in large part, a function of the residue's solvent accessibility as dictated by the conformation of the target protein. Therefore, this technique can be used to form an implicit picture of protein structure or conformation and to determine changes in conformation (i.e., tertiary and quaternary structure) that modify the accessibility of certain protein regions. Although the ways of modifying residues are diverse, and many have been in practice for over forty years, the advent of biomolecular mass spectrometry, employing electrospray and matrix-assisted laser desorption ionization (MALDI) and interfaced to liquid chromatography, makes possible highly specific, sensitive, and rapid analysis of modified peptides and proteins. See Fenn, et al., Science 246:64-71, 1989 and Karas et al., Anal. Chem. 57:2935-2939, 1985, the disclosures of which are hereby incorporated by reference in their entirety.

In-cell protein folding has been monitored using temperature jumps and Förster resonance energy transfer (FRET) between fluorescent proteins at the N- and C-termini of a protein of interest, providing important data on how the environments of different organelles can affect protein folding. This and other fluorescence based methods have better time resolution. However, like other fluorescent based methods which only provide data on the local environment around the fluorophore, the FRET-based method only reports on changes in end-to-end distances, and as with in-cell NMR based methods that measure protein stability and folding, it only reports on fully synthesized chains. See, for example, Ebbinghaus et al., Nat. Methods 7:319-323, 2010 and Smith et al., Curr. Opin. Struct. Biol. 30:7-16, 2015.

Protein oxidation by hydroxyl radicals is one class of footprinting methods; the various subclasses are differentiated by the means used to generate the hydroxyl radical (.OH). Hydroxyl radicals are useful for probing solvent accessibility because they have comparable size to solvent water molecules (and so proteins are accessible to hydroxyl radicals to a similar degree as water) and high reactivity with a significant fraction of amino acid side chains.

The advantages of hydroxyl radical footprinting are twofold. First, the primary sequence of modified residues is preserved by virtue of the stable (irreversible) covalent modification that occurs even though a protein may be subjected to several hours and even days of handling and proteolysis following the chemical footprinting step. Second, the hydroxyl radical is a reactive reagent, modifying many amino acid residues and affording a higher coverage footprint than those covalent approaches that target specific residues (e.g., the acetylation of primary amines). Hydroxyl radicals are highly unstable and reactive oxidation agents which very quickly oxidize a large variety of groups such as those present in amino acid side groups, adding a hydroxyl group and thereby increasing mass, which is detectable by mass spectrometry.

Fast photochemical oxidation of proteins (FPOP) is a mass spectrometry (MS)-based protein footprinting method. It uses a pulsed laser to photolyze hydrogen peroxide to generate OH radicals and modify proteins in a flow system on the microsecond timescale. The laser provides a spatially small, high flux of light, maximizing the exposure of a small volume of protein solution to hydroxyl radicals and ensures that the protein and hydrogen peroxide is irradiated only at the desired time and location.

The FPOP method probes the solvent accessibility of amino acid side chains by allowing accessible side chains to react with the hydroxyl radicals and become modified thereby. The side chains that are accessible, and therefore become modified, change upon ligand binding or alterations in protein conformation. The power of the method lies in comparisons between multiple states (e.g., ligand-free and ligand-bound states, or the conformation at different times during and after production). The differences in the oxidation pattern of the amino acid sidechains between multiple protein conformational states provides information on the structure of the protein and how it can change in response to ligand or other binding or conformational changes such as protein folding.

Although oxidation via hydroxyl radical induces unfolding in proteins on a timescale of milliseconds or longer, FPOP is designed to limit hydroxyl radical (.OH) exposure to 1 microsecond or less by employing a pulsed laser as an initiator to produce the radicals and a radical-scavenger to limit their lifetimes. When applying FPOP to three oxidation-sensitive proteins, it was found that the distribution of modification (oxidation) states is Poissonian when a scavenger is present, consistent with a single conformation protein modification model. This model breaks down when a scavenger is not used and/or hydrogen peroxide is not removed following photolysis. The outcome verifies that FPOP occurs on a time scale faster than conformational changes in these proteins. The labeled residues can be detected by standard proteolysis using trypsin or another protease, followed by LC/MS/MS, to provide information about the solvent accessibility of areas of the protein at the peptide and even the amino-acid level.

About fourteen out of twenty amino acids can be labeled upon laser exposure during FPOP with hydroxyl radicals. Their side chains are modified by reacting with .OH, with different amino acids exhibiting different rate constants and modification mechanisms. A typical side chain modification is the substitution of an —OH for —H, which results in the addition of 16 Da to the total mass of the protein. FPOP can be performed with other reagents as well. For example, sulfate radical cation and iodide radical reagents can be used. The iodide radical is considerably more specific than .OH, reacting with His and Tyr residues only.

The health of cells and organisms depend on functioning proteins, and the function of globular proteins is dependent on their ability to fold from a linear, one-dimensional chain of amino acids to a well-defined three-dimensional structure. Over the past five decades or more, protein folding studies have concentrated on the folding of full-length isolated chains in dilute solution where folding is dictated by the amino acid sequence. However, the intracellular environments are very different from dilute solution.

In cells, proteins are synthesized vectorially from the N— to the C— terminus and the elongating polypeptide chain interacts with the ribosome, molecular chaperones and modifying enzymes such as kinases, glycosyltransferases and protein disulfide isomerases. Cells are also crowded places, containing >200 mg/mL of various biomolecules. The vectorial nature of protein synthesis along with specific and non-specific interactions between the nascent polypeptide chain and its surroundings means that folding in the cell may differ from the folding of an isolated chain in solution.

SUMMARY OF THE INVENTION

Like other chemical footprinting techniques, FPOP can only provide accurate and unambiguous information about the time course of natural intracellular protein folding, if folding to the native, active conformation is interrogated. Therefore, there is a need in the art for methods that can ensure the environment under which the labeling occurs results in a native conformation, i.e. inside the cell. New tools such as those described herein for studying protein folding and quality control in cells are designed to better understand the normal functioning of cells, and environmental and other effects on protein folding such as aging or diseases from cancer to Alzheimer's disease.

The study of protein folding directly in the native cellular environment requires the development of new tools to provide higher resolution information than is currently available. To address this need, the present invention combines a pulse-chase technique with an in-cell protein footprinting method coupled with mass spectrometry to probe protein folding in cells. This method, entitled pulse-chase in-cell fast photochemical oxidation of proteins (pcIC-FPOP), provides information on short- and long-lived protein folding intermediates and interactions with chaperones in protein folding pathways in the natural environment of nascent proteins. The methods and apparatus of the invention allow a study of normal folding of proteins as it occurs inside the cell. The method also can be used to study any. mis-folding pathways to provide information helpful in designing drugs to block the. mis-folding pathway, hopefully leading to the correct fold and function of the protein. Techniques are provided for measuring in-cell protein folding.

In a first set of embodiments, an incubator includes a recess configured to receive a plate with multiple wells. The incubator also includes a removable cover for the recess. The cover is transparent to laser light of a first wavelength, which preferably is about 248 nm, and generally is within about 238 nm to about 270 nm, or about 240 nm to about 265 nm, or about 245 nm to about 250 nm. The incubator also includes a thermal source configured to supply heat to the recess, and a gas supply tube configured to supply a gas mixture including carbon dioxide and/or water vapor to the recess. For each well of the multiple wells, the incubator includes a set of perfusion tubes disposed to dispense and optionally withdraw fluid from a distal end at a position of the well. Each perfusion tube is configured at a proximal end to be in fluid communication with a corresponding reservoir outside the incubator. The pumps can be run in reverse to withdraw fluid from the well and send it back to the same or a different reservoir. In another embodiment, the pumps can withdraw fluid to a waste receptacle, using an appropriate valve system or other method known in the art.

In a second set of embodiments, a system includes the incubator of the first set of embodiments, and a laser source configured to emit a laser beam at the first wavelength. The system also includes a gas source for the gas mixture. Furthermore, the system includes a set of corresponding reservoirs and a plurality of pumps in fluid communication with the set of corresponding reservoirs. In addition, the system includes at least one processor; and at least one memory including one or more sequences of instructions. The at least one memory and the one or more sequences of instructions are configured to, with the at least one processor, cause the processor to control on or more components of a group of components comprising the laser, the thermal source, the gas source, and the plurality of pumps. In some of these embodiments, the memory and the instructions are further configured to, with the at least one processor, cause the processor to perform one or more steps of the following method.

In a third set of embodiments, a method includes obtaining cells in culture in the wells of the multi-well plate, which cells express the protein of interest; adding starving medium to these cells in culture (starving medium lacks arginine and lysine, see below); placing the multi-well plate in the incubator described above and positioning the incubator onto the stage for laser excitation. Next, the wells are simultaneously perfused with feeding medium (see below for additional information) that contains the same components as starving medium, but also contains arginine and lysine that optionally and preferably have been isotopically enriched or labeled with $^{15}$N. This perfusion is termed the pulse, and results in protein production where the proteins are labeled with $^{15}$N-arginine and $^{15}$N-lysine, for a first time period. After this pulse with labeled medium, all wells then are flushed with unlabeled feeding medium for a second time interval, which begins the chase. Individual wells then are subjected, at different times from the pulse, to treatment with hydrogen peroxide perfusion, irradiation with the laser, and quenching to stop the formation of hydroxyl radicals. Thus, a first well of the multi-well plate is perfused with a hydrogen peroxide solution, irradiated and quenched at a certain time; then a second well is perfused with a hydrogen peroxide solution, irradiated and quenched at a later certain time, followed by the same treatment of a third well, a fourth well, and so on until all wells have been subjected to the treatment. Each treated well thus results in a labeled population of protein molecules representing maturation and conformation of the proteins at the particular certain time, relative to the end of the pulse, when laser activation of the hydroxyl radicals occurs in the well.

The apparatus described above allows the multi-well plate to be contained in an incubator that maintains an appropriate temperature, humidity and $CO_2$ concentration for the cells, and allows the wells to receive, either simultaneously or individually the perfusion of the solutions and reagents used in the method. In addition, the stage on which the incubator is placed allows the laser to irradiate the wells being studied at the appropriate time, controlled by computer.

Once the testing is complete and all wells have been quenched, the multi-well plate is removed from the incubator and each well is tested by mass spectrometry after processing. The processing can include formation of a cell lysate from the contents of each well, such as, for example, collection of cell media from outside the cells and/or fractionation of the cells into a soluble cell lysate and an insoluble fraction containing membrane-bound components, aggregated proteins and cell debris from the contents of each well. After lysis, the samples optionally can be further processed by alkylation and reduction of cysteines, followed by acetone precipitation and digestion with a protease.

The samples then can be tested by any convenient means, such as by the following method. Preferably, digested peptides are separated on a C18 custom-packed column over a gradient from 3-45% acetonitrile. MS2 fragmentation using HCD can be carried out for identification of the peptides. In general, the samples are processed by any convenient method, such as by using a multi-level search strategy in Proteome Discoverer (Thermo Scientific™). The extent of oxidation can be calculated using a Power Pivot table in Excel™. The differences in oxidative labeling between the chase time points are used to determine when a region of the protein is solvent accessible (unfolded) and not solvent accessible (folded). Amino acids that are not solvent accessible will have lower level of oxidative labeling than when they are more exposed to solvent.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

Specifically, the invention relates to an incubator comprising a recess configured to receive a plate with a first plurality of wells; a removable cover for the recess, wherein the cover is transparent to laser light of a first wavelength; a thermal source configured to supply heat to the recess; a gas supply tube configured to supply a gas mixture including carbon dioxide and water vapor to the recess; and for each well of the first plurality of wells, a second plurality of perfusion tubes disposed to dispense fluid to or from a distal end at a position of each well, wherein each perfusion tube of the second plurality of perfusion tubes is configured at a proximal end to be connected in fluid communication with a corresponding reservoir outside the incubator. In preferred embodiments, in this incubator, each perfusion tube of the second plurality of perfusion tubes is configured at a proximal end to be in fluid communication with a corresponding infusion pump configured to move fluid to or from the corresponding reservoir into each well. In certain preferred embodiments, in this incubator, the second plurality of perfusion tubes comprises four perfusion tubes for each well of the first plurality of wells.

In certain embodiments, the incubator has a mass less than 500 grams and/or a maximum size dimension of less than 150 millimeters.

In some embodiments of the incubator, the first wavelength is about 248 nanometers and the cover comprises fused quartz silica.

In some embodiments, the incubator further comprises a controller for the thermal source connected by a communication line or a power line or both and/or a controller for air/gas and humidity connected by a communication line or a power line or both.

In other embodiments, the invention relates to a system comprising the incubator described herein; a laser source configured to emit a laser beam at the first wavelength; a gas source for the gas mixture; a second plurality of corresponding reservoirs; a plurality of pumps in fluid communication with the second plurality of corresponding reservoirs; at least one processor; and at least one memory including one or more sequences of instructions, the at least one memory and the one or more sequences of instructions configured to, with the at least one processor, cause the processor to control on or more components of a group of components comprising the laser, the thermal source, the gas source, and the plurality of pumps.

In other embodiments, the invention comprises an optical system comprised of mirror(s) and/or lenses referred to as beam steering optics. This optical system can be used to control the width and location of the laser beam to irradiate the individual wells of the multi-well plate, in one laser pulse or in multiple laser pulses per well.

In some embodiments of this system, the at least one memory and the one or more sequences of instructions are further configured to, with the at least one processor, cause the processor to perform at least the steps of:
  a. for a first time interval, operate at least one pump of the plurality of pumps to perfuse each well with fluid from a first reservoir of the second plurality of reservoirs;
  b. for a second time interval after the first time interval operate at least one pump of the plurality of pumps to perfuse each well with fluid from a different second reservoir of the second plurality of reservoirs;
  c. for a third time interval after the second time interval operate at least one pump of the plurality of pumps to perfuse a first well of the first plurality of wells with fluid from a different third reservoir of the second plurality of reservoirs;
  d. for a fourth time interval after the third time interval operate the laser source and/or the stage to illuminate the first well with the laser beam at the first wavelength;
  e. after the fourth time interval operate at least one pump of the plurality of pumps to perfuse the first well with fluid from a different fourth reservoir of the second plurality of reservoirs.

Preferably, in this system, the at least one memory and the one or more sequences of instructions are further configured to, with the at least one processor, cause the processor to repeat steps c, d, and e above for each remaining well of the first plurality of wells. In some embodiments of the system, the first reservoir holds feeding media that includes at least one amino acid labeled with a mass spectrometry label; the second reservoir holds feeding media that does not include the mass spectrometry label; the third reservoir holds hydrogen peroxide; and the fourth reservoir holds a quench solution.

In addition, the invention also relates to a method for determining the folding of a protein intracellularly, comprising (a) obtaining cells that express or overexpress the protein in the wells of a multi-well plate; (b) adding starving medium lacking arginine and lysine to the cell cultures in the wells of the multi-well plate; (c) placing the multi-well plate in an incubator that is configured with a recess to removably accommodate the multi-well plate and a removable UV transparent cover that to enclose the recess to allow a controlled environment in the recess; (d) positioning the incubator onto or into a stage in position for laser excitation and incubating the cells for 0 minutes to about 120 minutes, or any number of minutes sufficient for folding (which will be different for each protein tested); (e) perfusing all wells simultaneously with feeding medium that contains $^{15}$N-arginine, $^{15}$N-lysine, or a combination thereof, sufficient for detection by mass spectrometry, for a first time interval; (f) perfusing all wells simultaneously flushed with unlabeled feeding medium, for a second time interval; (g) perfusing one well with $H_2O_2$ for a third time interval and within about 1 second irradiating this well with a laser beam at a wavelength of about 238 nm to about 270 nm for a fourth time interval in order to produce hydroxyl radicals that react with exposed amino acid side chains on the proteins in the cells; (h) perfusing the one well of (g) with a quencher solution to quench the reaction of the hydroxyl radicals; (i) thereafter repeating steps (g) and (h) with each individual well of the multi-well plate at measured times until all wells have been perfused with $H_2O_2$, irradiated and quenched; and (j) removing the contents of each well individually, preparing a cell lysate sample of each well individually, optionally purifying or semi-purifying the cell lysate or other samples, and subjecting the cell lysate samples individually to tandem mass spectrometry to determine the location in the protein of amino acids that have been modified by reaction with hydroxyl radicals; and (k) analyzing the folding of the protein for each cell lysate sample, wherein the incubator includes at least one environmental supply that allows control of $CO_2$, humidity and temperature; wherein the incubator includes multiple perfusion tubes positioned with distal ends at the position of each well in the multi-well plate and proximal ends connected in fluid communication with one of multiple different external or internal reservoirs to infuse or withdraw fluid in each well; wherein the first time interval is sufficient to label an amount of protein detectable by tandem mass spectrometry, the second time interval (between the labeling pulse and the first/initial chase point, where the cells are exposed to unlabeled feeding medium) is 0 to about 10 minutes; and wherein the quencher solution preferably contains N-tert-butyl-α-phenylnitrone (PBN) and dimethylthiourea (DMTU).

In certain preferred embodiments, the method described herein involves positioning the incubator onto or into a stage in position for laser excitation and incubating the cells for 0 minutes to about 120 minutes, preferably about 20 minutes to about 100 minutes, more preferably about 20 minutes to about 60 minutes, and most preferably about 60 minutes in (d) and/or perfusing the well with $H_2O_2$ to achieve a concentration of about 20 mM to about 200 mM, in (g), and/or irradiating the well with a laser beam at a wavelength of about 240 nm to about 250 nm, and preferably about 248 nm in (g), and/or wherein the first time interval (where the cells are exposed to labeled feeding medium) is 0 to about 120 minutes (preferably less than one second to about 120 minutes or about 20 minutes to about 60 minutes, more preferably about 25 minutes to about 30 minutes, and most preferably about 30 minutes), the second time interval (where the cells are exposed to unlabeled feeding medium) is 0 minutes to about 10 minutes (preferably 0 seconds to about 60 seconds, more preferably 0 seconds to about 15 seconds, and most preferably 0 seconds to about 5 seconds, for example 0 seconds, 1 second, 2 seconds, 3 seconds or 4 seconds), the third time interval (where the cells are exposed to hydrogen peroxide prior to laser irradiation) is about 500 milliseconds to about 2 seconds (preferably about 500 milliseconds or about 1 second or about 1.5 seconds or about 2 seconds), and the fourth time interval (where the cells are irradiated by laser) is about 1 nanosecond to about 50 nanoseconds (preferably about 5 nanoseconds to about 30 nanoseconds, more preferably about 10 nanoseconds to about 20 nanoseconds, and most preferably about 15 nanoseconds to about 18 nanoseconds, for example, about 16 nanoseconds or about 17 nanoseconds). The time intervals between individual chase points can be any convenient times depending on the study, for example every 1-30 seconds, preferably about 1 second to about 15 seconds, or about 1 second to about 10 seconds, or about 1 second to about 5 seconds, or about 1 second to about 3 seconds, including about 2 seconds. The time intervals between chase points can be the same or different.

In a preferred embodiment, the method used a laser with beam steering optics to direct the beam through a first mirror that reflects the laser beam at an approximately 90° angle to a second mirror to irradiate the well.

In some preferred embodiments, the method for determining the folding of a protein intracellularly includes the analysis of the data resulting from mass spectrometry.

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

Figure 1:
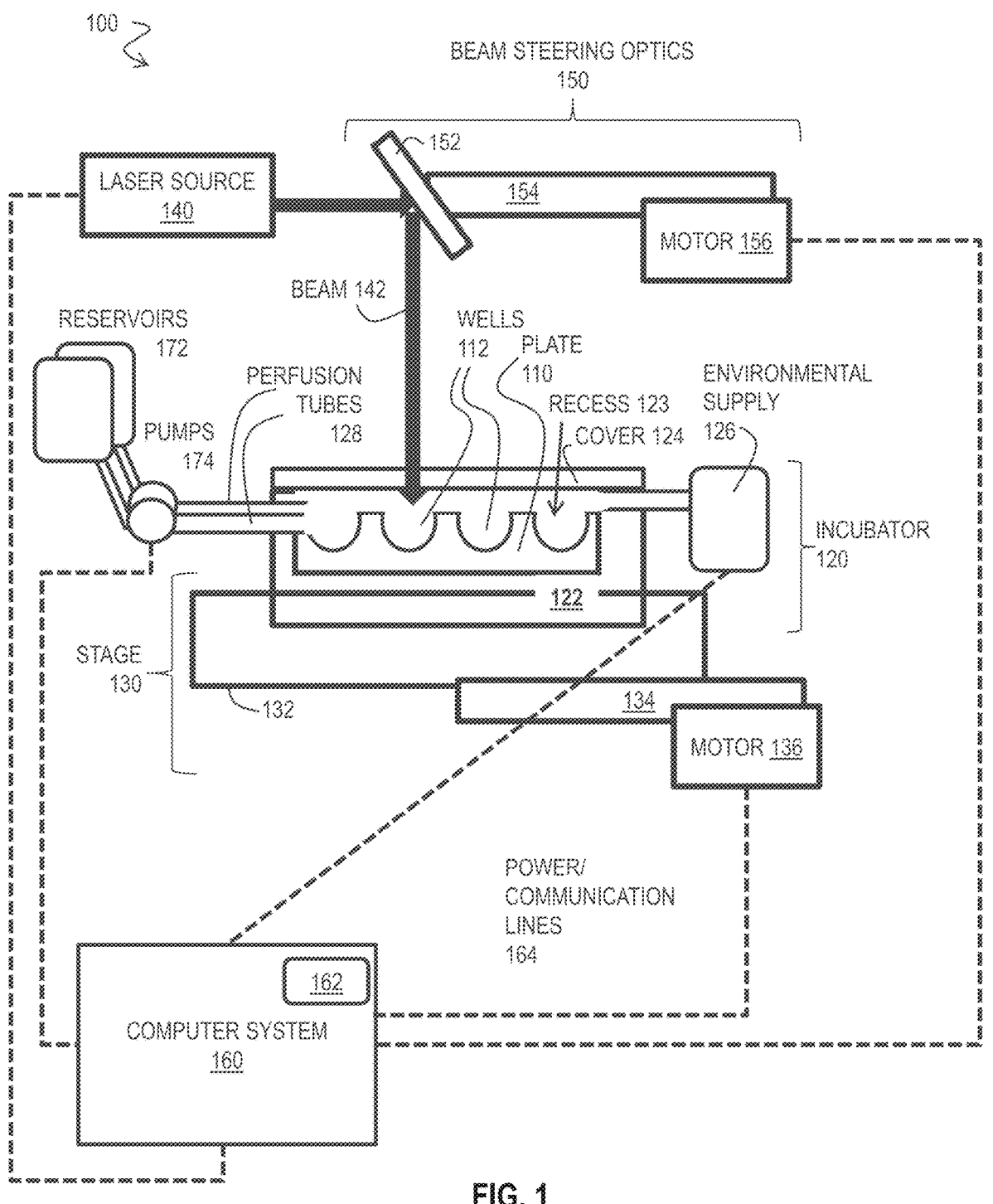
FIG. 1 is a block diagram that illustrates an example system for measuring in-cell protein folding, according to an embodiment.

A method and apparatus are described for measuring in-cell protein folding. In the following description, for the purposes of explanation, numerous specific details are set forth in order to provide a thorough understanding of the present invention. It is apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

As used herein, the term "starving medium" refers to a cell culture medium that contains nutrients and factors required and beneficial for maintenance of the cells in culture, but lacking lysine and arginine and having a low protein level. The exact components of the medium depend on the cells and can be determined easily by persons of skill in the art. For example, a preferred "starving medium" contains DMEM (Dulbecco's Modified Eagle Medium) or similar medium as is convenient and suitable for the cells under study, glucose and either no serum proteins or a low (about 0.5% wt/vol) concentration of serum proteins. The person of skill is well aware that different cells require different nutrients and other factors for optimal health, and can easily provide a suitable medium for the cells under study.

As used herein, the term "feeding medium" refers to a cell culture medium that contains the components of starving medium, but also contains lysine and arginine, and higher levels of serum proteins. The lysine and arginine optionally are isotopically enriched with $^{15}$N-lysine and $^{15}$N-arginine to provide a label detectable by mass spectrometry.

Some embodiments of the invention are described below, however, the invention is not limited to this context.

1. Overview

In various embodiments of this invention, a multi-well stage/incubator is used to maintain living cells during protein formation and measurements including labeling with a mass spectroscopic label and pulse-chase treatment. After the treatment is complete cell lysates from the individual wells are subjected to mass spectroscopy measurement to determine which peptides and amino acids of the protein in question are labeled with hydroxyl groups and therefore accessible in solution. Proteins are synthesized by the ribosome as one-dimensional chains of amino acids. As the protein folds over time into a complex, three-dimensional structure, amino acids that form contacts within the protein structure become less accessible to modification. Thus, the extent of modification and how this modification changes over time reports on protein folding. The operator therefore can gain information on the conformation and folding of the protein at different stages of protein production. The extent of oxidation can be quantitated from the LC-MS/MS data. In the unfolded protein, many amino acids will be exposed to solvent and will have a high level of labeling. As the protein folds, some residues will become buried and these will have a decreased level of labeling. When FPOP is performed at different time points, it is possible to determine the sequential steps in folding (i.e. which region folds first, which region folds second).

Studying in-cell protein folding requires a way to synchronize the population under study in order to follow folding over time. Pulse-chase experiments typically use the incorporation of radiolabeled amino acids into nascent proteins for this synchronization [33]. This is achieved by incubating cells with media containing radioactive amino acids, usually $^{35}$S labeled methionine and cysteine, for a set period of time called the pulse, changing the media and watching the maturation and trafficking of the radioactive protein over time, the chase (FIG. 1).

Radioactive (and non-radioactive) pulse-chase methods combined with immunoprecipitation of the protein(s) of interest provides information on disulfide bond formation, protein modifications such as glycosylation [35-37], interactions with the cellular quality control machinery including molecular chaperones [38-40], and protein trafficking [35, 36, 39] (for reviews see [12-14, 41]). These methods work particularly well for the secretory and integral membrane proteins produced in the oxidizing environment of the endoplasmic reticulum (ER). Approximately 30% of the human proteome consists of secretory and integral membrane proteins that fold and mature in the ER. While pulse-chase methods have provided important data on in-cell protein folding, maturation and trafficking, their molecular and temporal resolution is limited. For example, monitoring the compaction of a protein due to disulfide bond formation only reports on the regions near the disulfide bond and the temporal resolution of these methods tend to be minutes.

The development of the inventive apparati and methods for pcIC-FPOP are intended to overcome the limitations of currently available methods by providing both an increased molecular and temporal resolution. On the molecular level, FPOP's ability to oxidatively modify 17 of the 20 amino acids allows one to analyze the protein over its entire length. Further, hydroxyl radicals are highly reactive with hydrophobic residues with reactivity differences of 100-fold between residues such as Met, Leu, and Val and more polar residues such as Asp and Asn. This difference makes hydroxyl radical-based footprinting especially suited for studying protein folding where in more unfolded states hydrophobic residues are highly solvent accessible. As proteins fold, the solvent accessibility of these hydrophobic residues greatly decreases, leading to differences in the oxidation pattern. On the temporal level, FPOP oxidatively modifies proteins on the microsecond time scale allowing the study of transient interactions. This fast labeling permits the method to probe short-lived folding intermediates. Coupling IC-FPOP with pulse-chase experiments allows the investigator to synchronize newly synthesized protein populations. For the pulse, specifically $^{15}$N-labeled Arg and Lys amino acids are used to allow use of mass spectrometry-based quantitation method "stable isotope labeling with amino acids in cell culture" (SILAC) experiments.

The folding and maturation of the canonical secretory serpin $\alpha_1$-antitrypsin (A1AT) has been extensively studied in cells by other methods, as an isolated purified protein, and in folding simulations. At 394 amino acids, mature A1AT is also close to the median length of human proteins. A1AT is synthesized as a 418-amino acid long polypeptide, and the N-terminal 24 amino acid signal sequence is cleaved in the ER. In nature, the first 22 amino acids of functional A1AT are unstructured while the rest of the chain folds into the two-domain serpin structure containing a large $\alpha\beta$ sandwich domain and a mainly $\beta$ domain. A1AT also is an abundant secretory protein with normal concentrations of 1.5-3.5 mg/mL in human plasma with a turnover time of approximately 5 days, which means that hepatocytes, the major source of human A1AT, must make large quantities of this protein. These properties make A1AT a good candidate or model system for testing the inventive methods. See Example 4.

Figure 2:
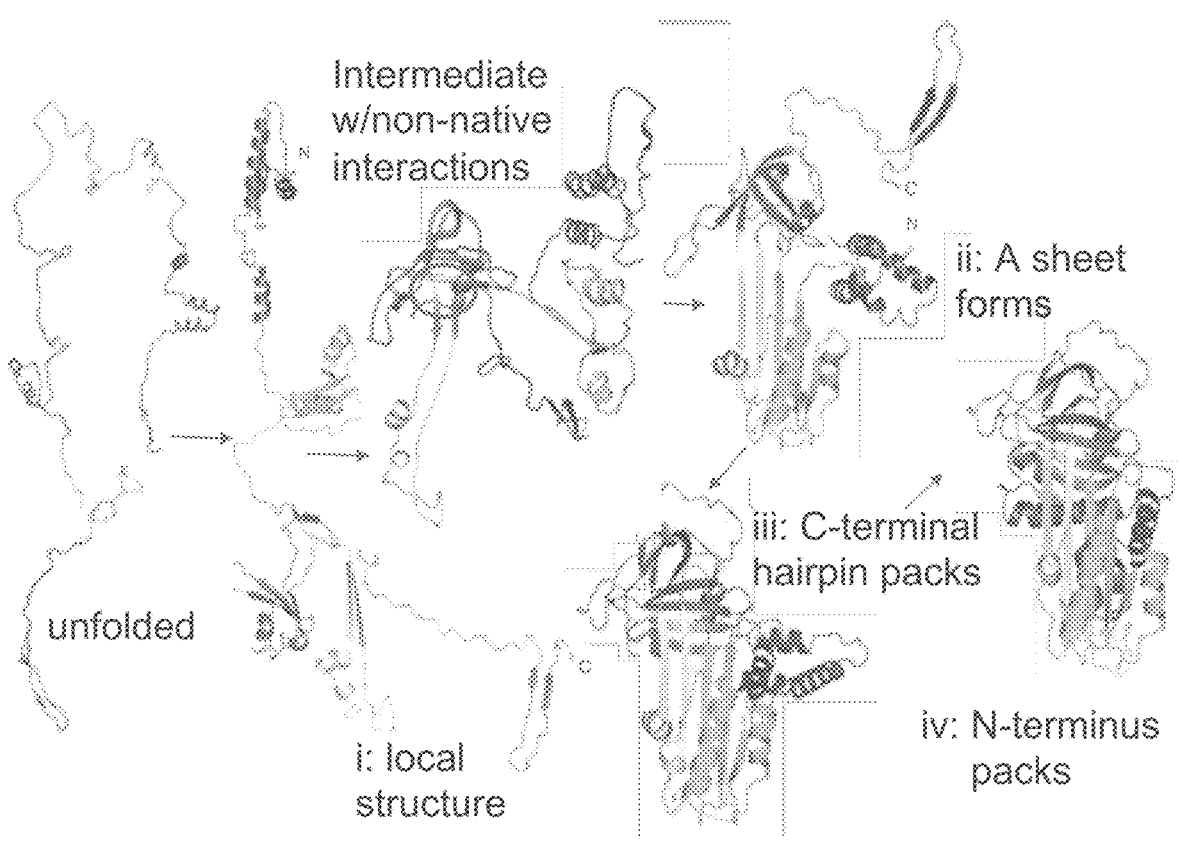
FIG. 2 is a cartoon showing successful wild-type A1AT folding from the simulations showing the (i) fast formation of local structure followed by folding to an intermediate with non-native interactions (see red circle), (ii) formation of the A sheet, (iii) packing of the C-terminus and finally packing of the N-terminus.

In vitro folding experiments, including FPOP studies of A1AT folding kinetics, along with folding simulations and in-cell experiments using prior art methods for A1AT and other serpins suggest a folding model with the major steps shown in FIG. 2. First, likely co-translational formation of dynamic local structure occurs in the N-terminal piece of the $\alpha\beta$ domain, particularly strands 2 and 3A and helix B and the N-terminal piece of the $\beta$ domain, particularly in strands 1 to 3B; second, docking of strand 5A to strand 3A to fully form sheet A which defines the $\alpha\beta$ domain occurs; third, insertion of the C-terminal hairpin formed by $\beta$ strands 4 and 5B into $\beta$ sheet B occurs; and fourth, docking of the N-terminal helices to the rest of the protein and final structure consolidation occurs. All of the major species in this folding model should be detectable by pcIC-FPOP. The Z mutant of A1AT has trouble forming the on-pathway non-native intermediate while in the milder S mutant of A1AT, slow consolidation of the mainly $\beta$ domain is likely the last step in folding. See FIG. 2.

For pcIC-FPOP to be an effective biophysical tool for studying in-cell protein folding, the method preferably should have certain characteristics. First, since protein folding can take place in the ER as well as in the cytoplasm and in mitochondria, the method needs to be able to oxidatively modify proteins in all of these cellular compartments. This issue has been addressed. See below, in Example 6. Second, in order to probe short-lived intermediates in the folding pathway, the method preferably is able to probe cellular samples at various chase points that may be as short as a few seconds or as long as several minutes. This has been described herein. Third, the efficacy of the method preferably should be validated using a model protein system. Finally, the method is sensitive enough to detect mis-folding proteins.

Figure 7A:
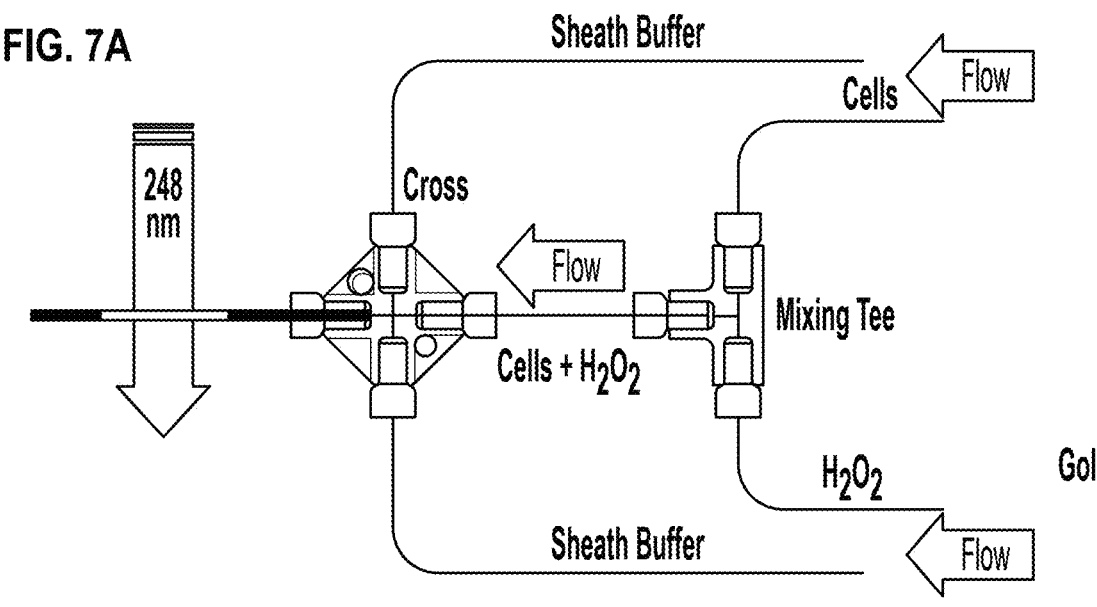
FIG. 7A is a cartoon showing a prior art single cell flow platform; the use of a sheath buffer allows cells to flow toward the laser in a single line.

To monitor protein folding as it occurs in the cell by pcIC-FPOP in an embodiment of the invention, cells are oxidatively modified at varying times after the isotopic label pulse. Experimental measurements have demonstrated that proteins fold on the millisecond to second timescale, so fast analysis is required for protein folding studies. The currently available IC-FPOP platform uses a flow system to flow cells through the laser beam (FIG. 7A). The analysis of each sample is 10 minutes with an additional 10 minutes for washing the flow system between samples. This time is too long to detect short-lived folding intermediates where each sample is a different chase time point. The IC-FPOP platform according to the invention is designed to allow for analysis of a static cell sample rather than a flowing one and can capture protein morphology on a very small time scale. The multi-well plate is used for pulse chase treatment of cells, including those transiently transfected with the protein of interest and each well is used as a different chase time point.

For pcIC-FPOP methods according to the invention, it is highly preferable that the cells used in the study are incubated at optimal cell culture conditions for at least the time period of the testing, so that normal cellular functions, particularly protein synthesis, are maintained. The temperature, humidity, and $CO_2$ concentration can be controlled on the stage top incubator, which is designed for live cell imaging. To ensure the stage top incubator conditions are amenable for cell culture at the laser platform, transient transfections can be tested in the incubator, for example using the chimeric protein GCaMP2 as a model system. GCaMP2, a fluorescent protein used as an intracellular calcium indicator, is a fusion of green fluorescent protein (GFP) and calmodulin. The protein is highly fluorescent when calcium is bound and its fluorescence is reduced in the absence of calcium. Owing to its fluorescent properties, the protein is a good model system to test cellular function. Transient transfections of GCaMP2 were used as a marker for the suitability of the stage top incubator for maintenance of healthy cells. See Example 4.

Coupling FPOP with high resolution tandem MS allows interaction sites to be identified on the amino acid-residue level. The method has been used in vitro to identify protein-protein and protein ligand interactions as well as regions of protein conformational change. This invention for the first time extends the FPOP method to in-cell analysis of protein folding.

Embodiments of the invention described and claimed herein extend the use of IC-FPOP for studying protein folding by coupling the method with the pulse-chase technique in cells. This method allows the study of protein folding pathways on the amino acid residue-level, a resolution that is much higher than currently available methods. The method development requires the redesign of the IC-FPOP platform to increase the analysis speed of the method. This enables the study of short-lived intermediates. In addition, by using $\alpha_1$-antitrypsin (A1AT) as a model system, the conditions for pcIC-FPOP can be optimized. Embodiments of the invention also can be used to analyze protein misfolding by analyzing mutants of A1AT with varying degrees of severity of consequences.

This specification describes the development of a novel method to analyze protein folding in-cell, which would fill a gap in technology in understanding how the cellular milieu impacts protein folding. Studying in-cell protein folding requires a way to synchronize the population in order to follow folding over time. Pulse-chase experiments typically use the incorporation of radiolabeled amino acids into nascent proteins for this synchronization. This is achieved by incubating cells with media containing radioactive amino acids, usually $^{35}S$ labeled methionine and cysteine, for a set period of time called the pulse, changing the media and watching the maturation and trafficking of the radioactive protein over time, the chase.

2. Apparatus and System

FIG. 1 is a block diagram that illustrates an example system 100 for measuring in-cell protein folding, according to an embodiment. The system 100 includes a multi-well plate 110, an incubator 120, a stage 130, a subsystem of reservoirs 172 and pumps 174, a laser source 140 and beam steering optics 150, and a computer system 160 programmed with a control module 162 to control the operation of the laser 140, optics 150, incubator 120, stage 130, or pumps 174, or some combination. Although FIG. 1 depicts one optical coupler 152 in the beam steering optics, a preferred embodiment uses two mirrors to focus the laser in a downward direction onto the well 112 of the multi-well plate 110.

The plate 110 includes multiple wells 112 so that a different pulse-chase reaction can be instituted in each well 112. In various embodiments, the number of wells 112 in one plate 110 is greater than two, and is advantageously six or more wells 112 in a single plate 110. The more wells, the more different closely timed stages of protein formation can be detected in a single experiment, and thus, the greater is the temporal resolution of protein formation that can be determined in one set of tests.

The incubator 120 includes a frame 122 that is configured with a recess 123 to removably accommodate the multiwalled plate 110. The incubator includes a removable cover 124 that encloses the recess 123 so that a controlled environment can be established in the recess 123, for the benefit of any cells cultured in the wells of any plate inserted into the recess. The cover 124 is transparent to the wavelength of light to be used to excite a reaction (e.g., hydroxyl production) during the measurements. The incubator includes an environmental supply 126, which provides the temperature and gas for the controlled environment. In various embodiments, the environmental supply includes a heat source for controlling the temperature in the recess, and a supply of carbon dioxide or water vapor or both, to control the air and humidity. In some embodiments, the gas and water supply are external to the incubator, in some embodiments, one or more are integrated within the incubator.

Unlike incubators previously in use, the incubator 120 includes multiple perfusion tubes 128 positioned with distal ends at the position of each well 112 in the multi-well plate 110 having more than two wells to be enclosed by the incubator 120. The number of perfusion tubes with distal ends at each well position is three or more. The proximal end of each perfusion tube reaches outside the frame 122 and is configured to be connected in fluid communication with one of multiple different external or internal reservoirs 172. The perfusion tubes are configured to infuse and/or withdraw fluid in each well based on the operation of internal or external pumps 174 into or out of reservoirs 172. The system 100 includes the pumps 174 and reservoirs 172 for incubator 120.

The system includes a laser source 140 and beam steering optics 150 configured to direct a beam 142 of light from the laser source through the transparent cover 124 and onto one well at a time. The laser beam 142 is used to excite a reaction (e.g., hydroxyl radical production) during the measurements. The beam steering optics 150 include one or more optical couplers 152. As used herein, an optical coupler is any component that affects the propagation of light within spatial coordinates to direct light from one component to another component, such as a vacuum, air, glass, crystal, mirror, lens, optical circulator, beam splitter, phase plate, polarizer, optical fiber, optical mixer, among others, alone or in some combination.

In some embodiments, the beam steering optics 150 includes one or more motors 156 connected by linkage 154 to one or more optical couplers 152. For example, in some embodiments, an electric rotating motor 156 is connected along an axis 154 of a rotating polygonal mirror 152 that repeatedly changes the angel of the beam 142 through a small range of angles. One way to accomplish this is to use a mirror and a scanning galvanometer system, for example a large beam diameter dual-axis scanning galvo system from Thorlabs™.

The system includes a stage 130 for holding the incubator in position relative to the laser beam 142. The stage 130 includes a cradle 132 that is configured to receive the incubator 120. In some embodiments, the stage 130 includes a motor 136 and linkage 134 connected to the cradle 132 and configured to move the frame in one or two or three dimensions relative to the laser beam 142. In an example embodiment, described in more detail below, the linkage 134 is a two dimensional (2D) moving platform operated by a nanometer stepping motor.

At successive times, the beam is directed onto another well, either by using motor 156 to reorient the beam 142 or by using motor 136 to move the cradle 132, or both.

The system 100 includes computer system 160, such as the computer system described below with respect to FIG. 5 or chip-set described below with reference to FIG. 6. The computer system 160 is in electronic communication with one or more of motor 136, motor 156, pumps 174, environmental supply 128 or laser source 140 via wired or wireless communication lines or power lines or both, represented by dashed lines 164. The computer system 160 includes a control module 162 configured in hardware, firmware, or software, or some combination, to control the laser 140, motors 136 and 146, pumps 174 and environmental supply 128 to effectuate one or more steps of a method involving living cells, the laser, and the chemical environment of the cells. In some embodiments, the control module 162 is configured to perform a method to determine the folding state of proteins during cell processes, including protein formation, as described in more detail below with reference to FIG. 3. For example, in some embodiments, the control module 162 controls the positioning system, each individual pump channel, and the laser in one software module. A script builder allows for the control of each channel on a pump individually. The sequence builder allows for input of each part of the platform and their timing (e.g. laser pulse start).

Although modules and equipment are depicted in FIG. 1 as integral blocks in a particular arrangement for purposes of illustration, in other embodiments one or more modules or equipment or structures, or portions thereof, are arranged in a different manner, or are omitted, or one or more different modules and equipment and structures are included.

In an embodiment, the system 100 is configured for in cell (IC) fast photochemical oxidation of proteins (FPOP) uses hydroxyl radicals to oxidatively modify proteins and determine time evolution of same using pulse-chase techniques. Different pulses are initiated at different times in different wells. In these embodiments, described in more detail below, there are four perfusion tubes for each well position. A first perfusion tube for each well position is connected via one or more pumps to one or more reservoirs of mass spectroscopy labeled feeding media. If there are three wells, then there are three first perfusion tubes connected to that one or more reservoirs of labeled feeding media. If there are four wells, then there are four first perfusion tubes connected to that one or more reservoirs; if five then five, etc. A different second perfusion tube for each well position is connected via one or more different pumps to one or more different reservoirs of unlabeled feeding media. A different third perfusion tube for each well position is connected via one or more different pumps to one or more different reservoirs of hydrogen peroxide ($H_2O_2$). A different fourth perfusion tube for each well position is connected via one or more different pumps to one or more different reservoirs of quenching medium. In some embodiments, measurements are not so sensitive; and, the same perfusion tube can be used for multiple different fluids.

The pumps are activated under control of control module 162 to successively flush each cell with one of the fluids and can withdraw the fluid, or fluid mix, at a later time, if desired. At a certain stage of fluid infusion or withdrawal, the laser source 140, or beam steering optics 150, or stage 130, or some combination, is operated by control module 162 to illuminate a well or portion thereof to produce hydroxyl radicals in the well and inside cells that have taken up hydrogen peroxide. At different times the laser beam 142 is directed by control module 162 into a different well or portion thereof.

3. Method

Figure 4:
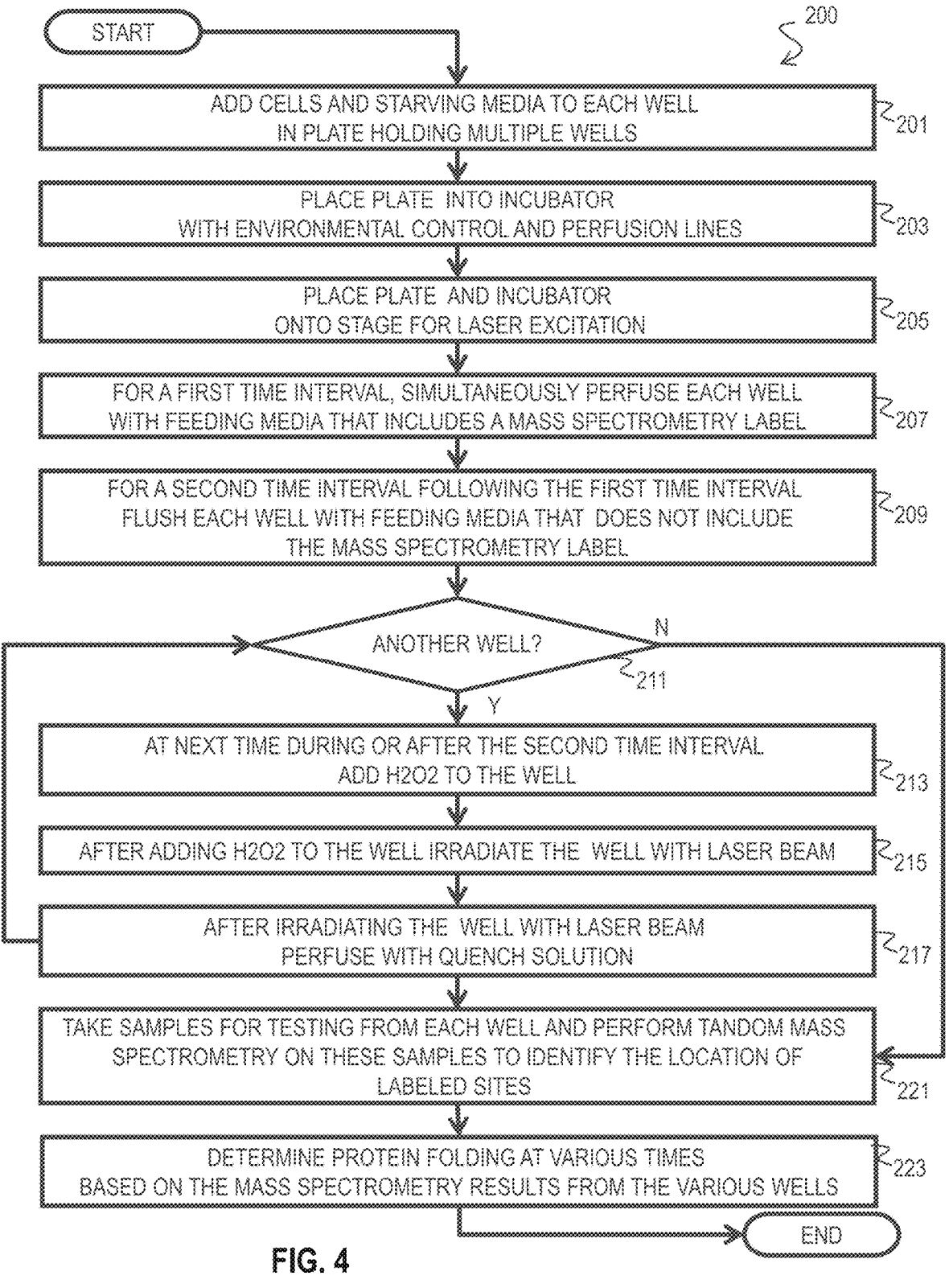
FIG. 4 is a flow diagram that illustrates an example method for measuring in-cell protein folding, according to an embodiment.

FIG. 4 is a flow diagram that illustrates an example method for measuring in-cell protein folding, according to an embodiment. Although steps are depicted in FIG. 4 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 201, one or more cells expressing the protein to be studied and starving medium (medium lacking arginine (Arg) and lysine (Lys)) are added to one or more wells 112 of the plurality of wells 112 of a multi-well plate 110. For some IC FPOP pulse-chase experiments, each well 112 is intended to determine the folding of proteins at a later stage of protein formation after exposure to a feeding medium. In other embodiments, each well 112 is used for a different cell type or protein process, such as during a particular chemical reaction inside the cell.

In step 203, the multi-well plate 110 is placed into the incubator 120 with environmental control and perfusion lines connected to the individual wells.

In step 205, the incubator 120 containing the plate then is placed onto or fitted into the stage 130 in position for laser excitation. In certain embodiments, the incubator optionally remains in this position for a period of time prior to the next step so that the cells in the wells can be monitored. This time period is from a few minutes to several hours, specifically from 0 minutes to 120 minutes, preferably about 20 minutes to about 100 minutes, more preferably about 20 minutes to about 60 minutes, and most preferably about 60 minutes.

In step 207, for a first time interval, all wells 112 are perfused simultaneously with feeding medium that includes a mass spectrometry label. The feeding medium contains the nutrients and other factors required for compatibility with cellular life as in the starving medium, and also contains a mass spectrometry label, preferably isotopically enriched $^{15}N$-Arg, $^{15}N$-Lys, or a combination thereof, sufficient for detection by mass spectrometry. Any convenient and stable isotopic label for mass spectrometry can be used. The time interval for the perfusion with the label is from 0 minutes (or less than 1 second) to 120 minutes, preferably about 20 minutes to about 60 minutes, more preferably about 25 minutes to about 30 minutes, and most preferably about 30 minutes.

In step 209, in a second time interval following the perfusion with labeled feeding medium, each well 112 is simultaneously flushed with unlabeled feeding medium prior to the first or initial chase point. This time interval has a duration of from 0 minutes to about 10 minutes, preferably from about 0 seconds to about 60 seconds, more preferably about 0 seconds to about 15 seconds, and most preferably about 0 seconds, or less than one second, or two seconds.

In step 211, the operator determines whether a well 112 that has not been subjected to step 213 remains in the multi-well plate. If there is no remaining well 112, the operator proceeds to step 221. If there is a remaining well 112 that has not been subjected to step 213, the operator proceeds to step 213 for this well.

In step 213, $H_2O_2$ is added to an individual well 112, during or after the second time interval, the $H_2O_2$ is added to achieve a concentration of about 20 mM to about 200 mM $H_2O_2$ in the well 112, preferably about 50 mM to about 150 mM, and more preferably about 100 mM or 200 mM.

In step 215, after adding the $H_2O_2$ to the individual well 112 (preferably about 1 second after adding the $H_2O_2$), the individual well 112 is irradiated with a laser beam at about 238 to about 270 nm, preferably 248 nm, for a duration of about 1 nanosecond to about 50 nanoseconds, preferably about 5 nanoseconds to about 30 nanoseconds, more preferably about 10 nanoseconds to about 20 nanoseconds, and most preferably about 15 nanoseconds to about 18 nanoseconds or about 17 nanoseconds in order to produce hydroxyl radicals that react with amino acid side chains that are accessible in solution at the time the hydroxyl radicals were available.

In step 217, after irradiating the well (preferably immediately after irradiating the well or less than a few milliseconds or less than one second after irradiating the well), the individual well 112 is perfused with a quench solution to stop the reaction and capture the labeling at that time point after the pulse. The quench solution contains about 100 mM to about 200 mM each of PBN and DMTU, preferably about 120 mM to about 150 mM each of PBN and DMTU, more preferably about 120 mM to about 125 mM, and most preferably about 125 mM.

In step 221, samples of each individual well 112 (preferably cell lysate samples) are taken and subjected to tandem mass spectrometry to identify the location of amino acid side chains that have reacted with the hydroxyl radical in those wells 112.

In step 223, the protein folding is determined for each sample, thereby determining the protein folding at the times labeling with hydroxyl radicals occurred.

The steps of FIG. 4 are conveniently conducted on the system 100 of FIG. 1, by having four perfusion tubes terminate over each well 112 of a multi-well plate 110 and connected by corresponding separately controlled pumps for each well 112 to four reservoirs 172 holding a labeled feeding medium, unlabeled feeding medium, hydrogen peroxide, and a quenching medium, respectively.

4. Example Embodiments

Figure 3A:
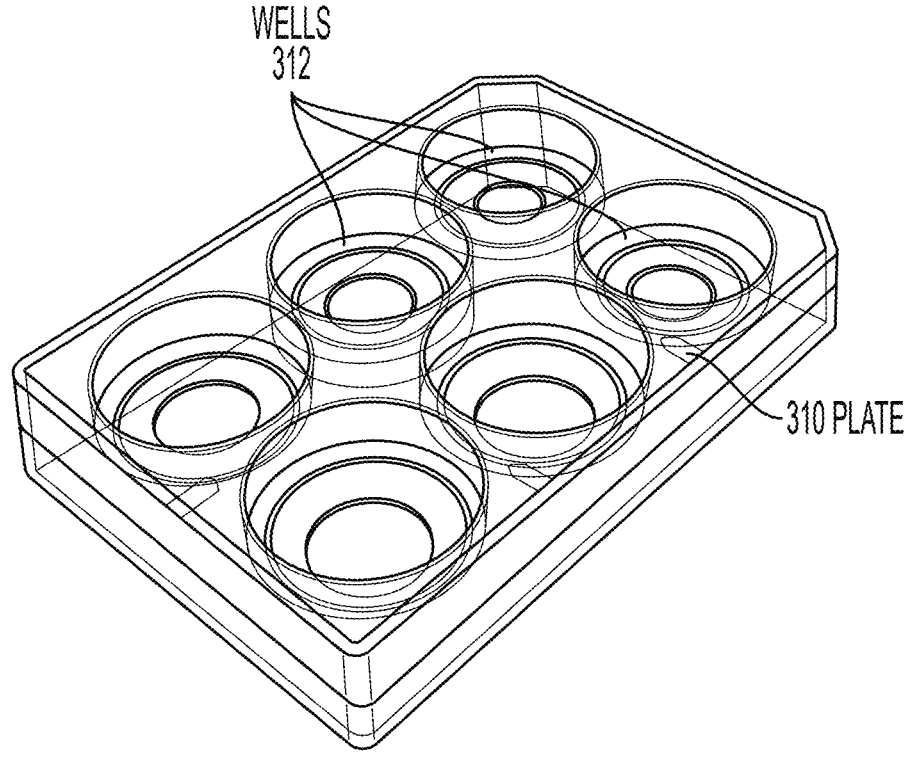
FIG. 3A through FIG. 3E are block diagrams that illustrate an example system, according to an experimental embodiment.

FIG. 3A through FIG. 3E are block diagrams that illustrate an example system, according to an experimental embodiment. FIG. 3A is a perspective drawing that illustrates an example plate 310 with six wells 312, according to an experimental embodiment. Each well is configured to hold cells and inter-cellular fluids. Such a plate is suitable for determining protein folding at six different times during protein formation.

Figure 3B:
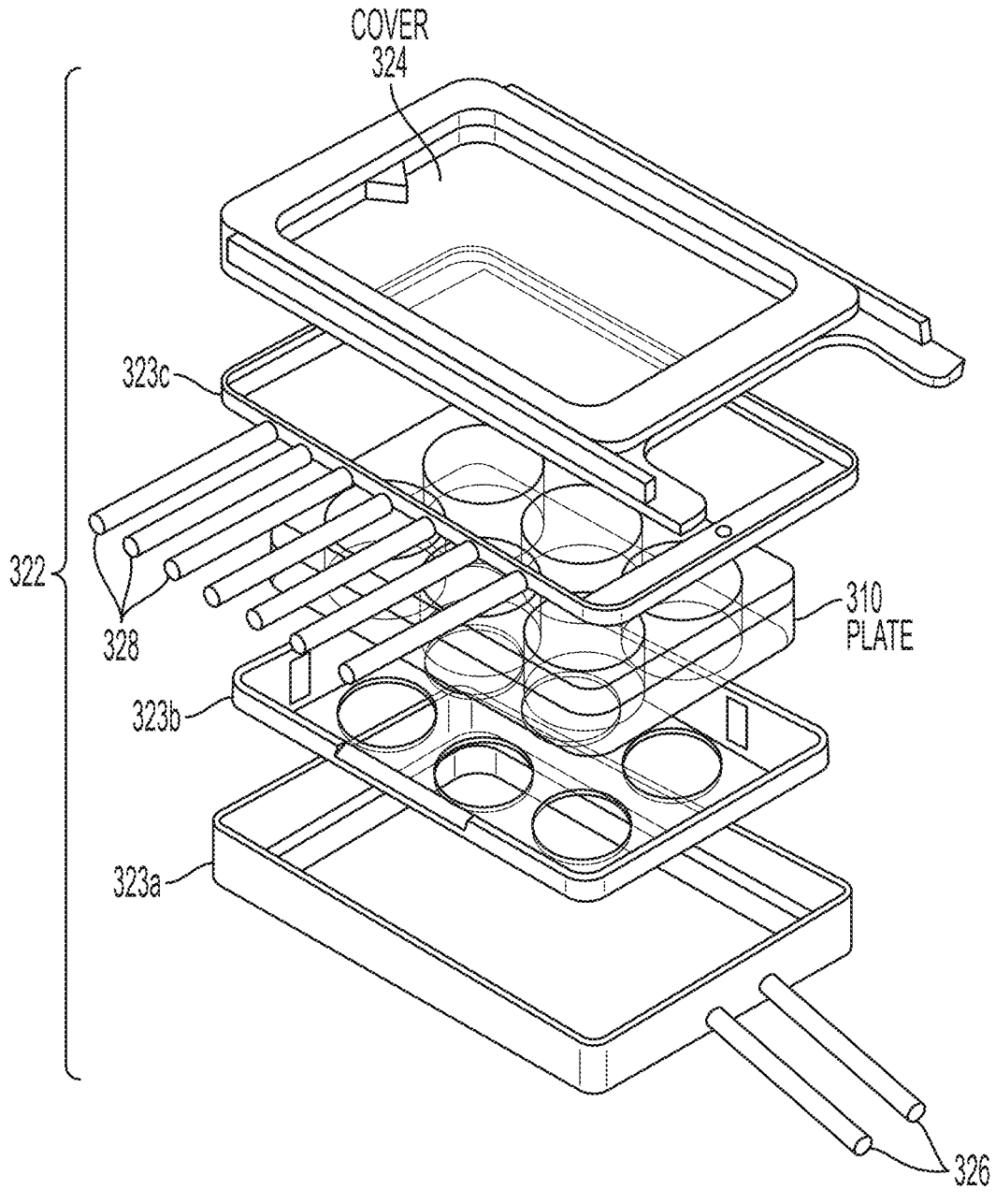

FIG. 3B is block diagram of an exploded view of an example incubator frame 322, according to an experimental embodiment FIG. 3B illustrates enclosure of the plate 310 into a recess of the incubator frame 322. The incubator frame 322 includes an incubator base 323a, a plate support 323b, and a tube support 323c. After the plate 310 is placed on the support 323b, an incubator cover 324, transparent to a wavelength of light to be used to release hydroxyl ions from hydrogen peroxide, is placed over the plate 310 and tube support 323c. The incubator base includes lines 326 for the supply of thermal power, air and humidity used in common by all cells in all wells. The tube support 323c, fixes the distal ends of multiple perfusion tubes 328 at positions over each well on the six-well plate, as described in more detail below.

A schematic of the incubator for a 6-well plate, which is a preferred configuration for pcIC-FPOP, is shown in FIG. 3B. Although a similar 6-well plate configuration is available from Okolab™ as discussed above, to make the incubator compatible with pcIC-FPOP several modifications have been made to the traditional design. Instead of four perfusion lines, the custom incubator has six lines per well for a total of 36 lines. This modification is required to control media addition and removal, $H_2O_2$ addition, and quench solution addition to each well. Also, since the wavelength of the laser preferably is 248 nm, the standard glass lid would absorb a significant amount of the laser beam. To overcome this, the custom incubator has a lid made of fused quartz silica. This is the same material used for the flow tubes in in vitro FPOP and IC-FPOP. The incubator has connections to a temperature control unit and a humidity and $CO_2$ control unit. This allows the cells to be maintained at optimal conditions for preserving function, including protein synthesis, at the laser platform. For example, in some embodiments, the stage top incubator is completely enclosed and kept at 37° C. with 5% $CO_2$.

Figure 3C:
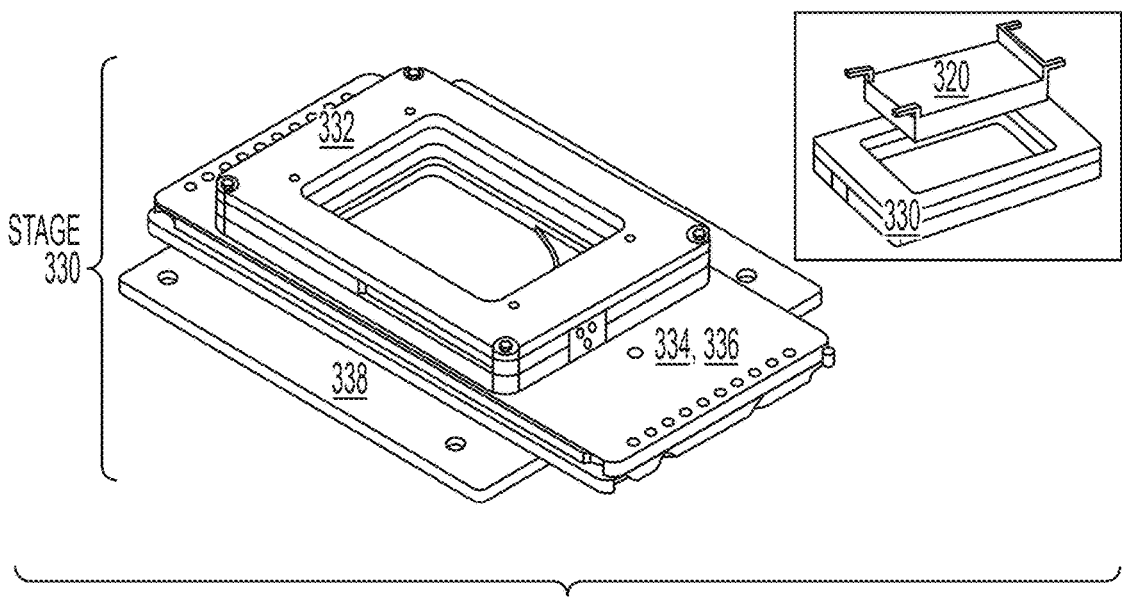

FIG. 3C is a block diagram that illustrates an example stage 330, according to an experimental embodiment. The stage 330 is made up of a base 338 that can be fixed to an experimental surface in view of a laser source. Attached to the base is a two-dimensional moving platform motivated by one or more nano-stepping motors (internal and not shown) to incrementally change position of a top surface of the platform in two dimensions (two horizontal perpendicular directions) relative to a laser source. The platform 334 serves as linkage 134 in this embodiment. On the top surface of the moving platform 334 is fixed an incubator cradle 332 configured to hold the incubator frame 322 of FIG. 3B, as shown in the insert.

Stage top incubators generally are used for live cell microscope imaging applications. These incubators allow control of temperature, humidity, and $CO_2$ gas concentration so that cells can be maintained in an amenable environment for growth. An example of a standard stage top incubator is sold by Okolab™. This incubator holds two 35 mm dishes, has four perfusion lines for introducing and removing liquids to each dish, and has connections to a temperature control unit and a $CO_2$ and humidity control unit.

In preferred embodiments, in order to move the stage top incubator so that each well can be exposed to a stationary laser light, a nanopositioning system is included. The Nano-LPMW system, made by Mad City Labs™, is a high speed nanopositioning system that can travel in the X, Y, and Z dimensions. FIG. 3C shows the schematic of the system custom designed for pcIC-FPOP. The system has a base plate that allows it be screwed into the optical table on which the laser is located. The aperture, which is much larger than the standard system sold by Mad City Labs™, is designed to accommodate the multi-well stage top incubator (FIG. 3C, inset). This design also allows for an increased range of motion, compared to standard systems, to account for the dimensions of a multi-well plate. The incubator and nanopositioning instruments preferably are fully compatible with each other and with the needs for pcIC-FPOP. Given the 450 g estimated weight of the stage top incubator, the response time of the nanopositioning system is estimated at 50-60 milliseconds. This can be tested and confirmed using a load of 450 g to ensure that the movement is as fast as possible. The movement of the nanopositioning system is controlled by computer software. In other embodiments, the stage does not move during use, but rather the laser or a system of mirrors and lenses or other optical devices control the laser for irradiation of the wells of the multi-well plate.

Perfusion lines on the stage top incubator permit solutions to flow in and out of each well, which requires several peristaltic pumps. For perfusion, four 4-channel Reglo™ ICC pumps are used. Each of the channels on the pump can operate independently with various flow rates in infusion or withdraw modes. With four pumps, there are a total of 16 independent channels which is sufficient for pcIC-FPOP as described above.

Figure 3D:
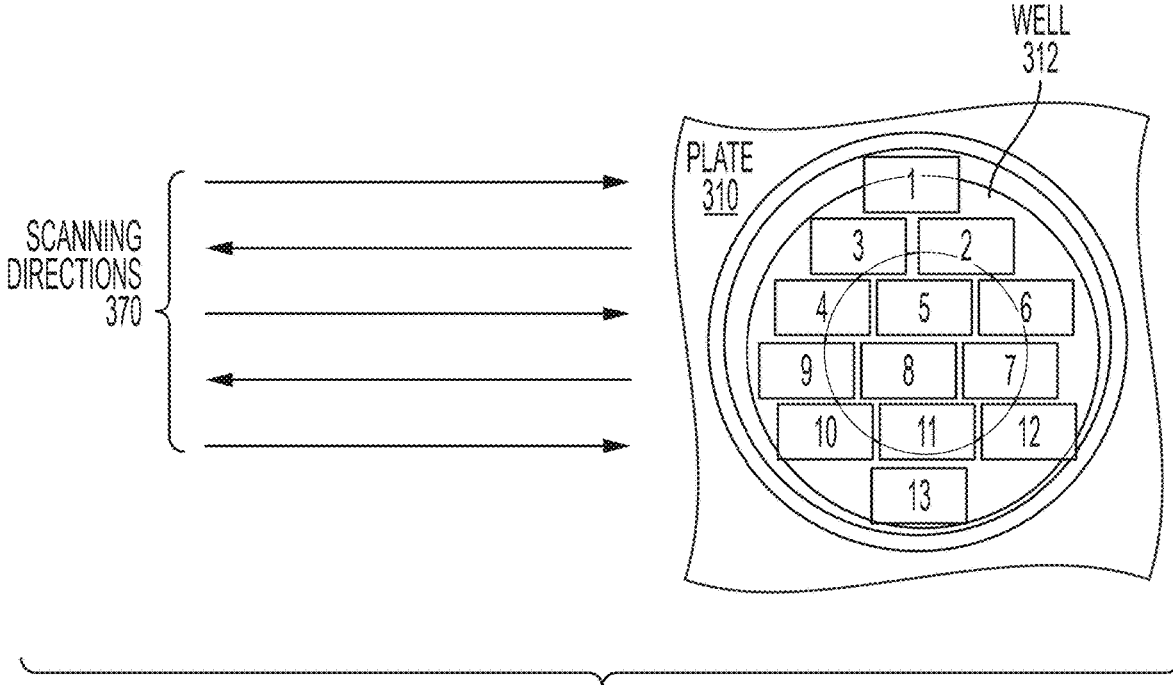

FIG. 3D is a block diagram that illustrates an example sequence of scanning directions of the laser past the stage for one well 312 on plate 310 with 13 numbered sections that are illuminated separately by a laser (not shown), according to an experimental embodiment. In this embodiment, the laser beam is stationary; and the entire scan is accomplished by movement of the platform 334. In another embodiment, the laser beam is steered using one or more of a combination of optical couplers to irradiate a portion of the well or the entire well. Preferably, two mirrors, such as excimer laser line mirrors are used to reflect the entire beam. See further discussion below, with respect to Example 3.

The nanopositioning system is used to move the stage top incubator so that each well is exposed to irradiation from a stationary laser. Since the laser beam is static and moving the bulky laser would be difficult, the multi-well plate moves, in this embodiment. The width of the laser beam, which is 3.5 mm, is too small to irradiate an entire well at once in some embodiments. However, widening the beam to the size of an individual well may lead to decreased laser intensity and a reduction in hydroxyl radical production. For example, in the application of a nanosecond laser photolysis footprinting method on cells in a well plate, Zhu et al. [53] showed that increasing the width of their laser beam to irradiate an entire well in one shot reduced their beam intensity by 30-fold.

Therefore, rather than losing laser beam intensity with an increased beam width, the well can be rapidly scanned with multiple irradiations per well. As demonstrated in FIG. 3D, for this embodiment the nanopositioning system moves the multi-well plate in such a manner as to cause the laser beam to cross a single well rapidly in a continuous motion to irradiate the entire well using multiple pulses (FIG. 3D). The width of the laser beam can be increased slightly using a lens so that only 13 shots of the laser per well are required. This reduces the time required to irradiate an entire well while only slightly reducing the laser intensity. In other embodiments, the laser beam is moved across the well in the same pattern.

Preferably, in IC-FPOP studies, the energy of the laser is set at 160-170 mJ. However, the KrF laser has a maximum energy capability of 250 mJ. Therefore, although a 30-fold decrease in laser energy for a beam wide enough to irradiate an entire well cannot be accommodated, a slight increase in laser beam width can be compensated for by an increase in laser energy. The laser has a maximum frequency of 50 Hz (0.02 s) so 13 laser pulses per well can be achieved in a short period of time (26 ms). The rate-limiting step is the response time of the nanopositioning system which at 50 ms, should allow for an entire well to be irradiated in about 650 ms. This speed allows for multiple chase time points to be tested on a time scale that is appropriate for studying protein folding. Other lasers and positioning systems can, of course, be used with the invention.

Alternatively, it is possible to widen the beam width enough to require only 6 laser shots (movements) across the well. This should only reduce the beam intensity a small amount which may be compensated for by increasing the laser energy. In addition, the laser beam can be widened to fill the entire width of the well and the $H_2O_2$ concentration increased to ensure enough radicals are generated to oxidatively modify proteins to a detectable degree within the well.

Figure 11:
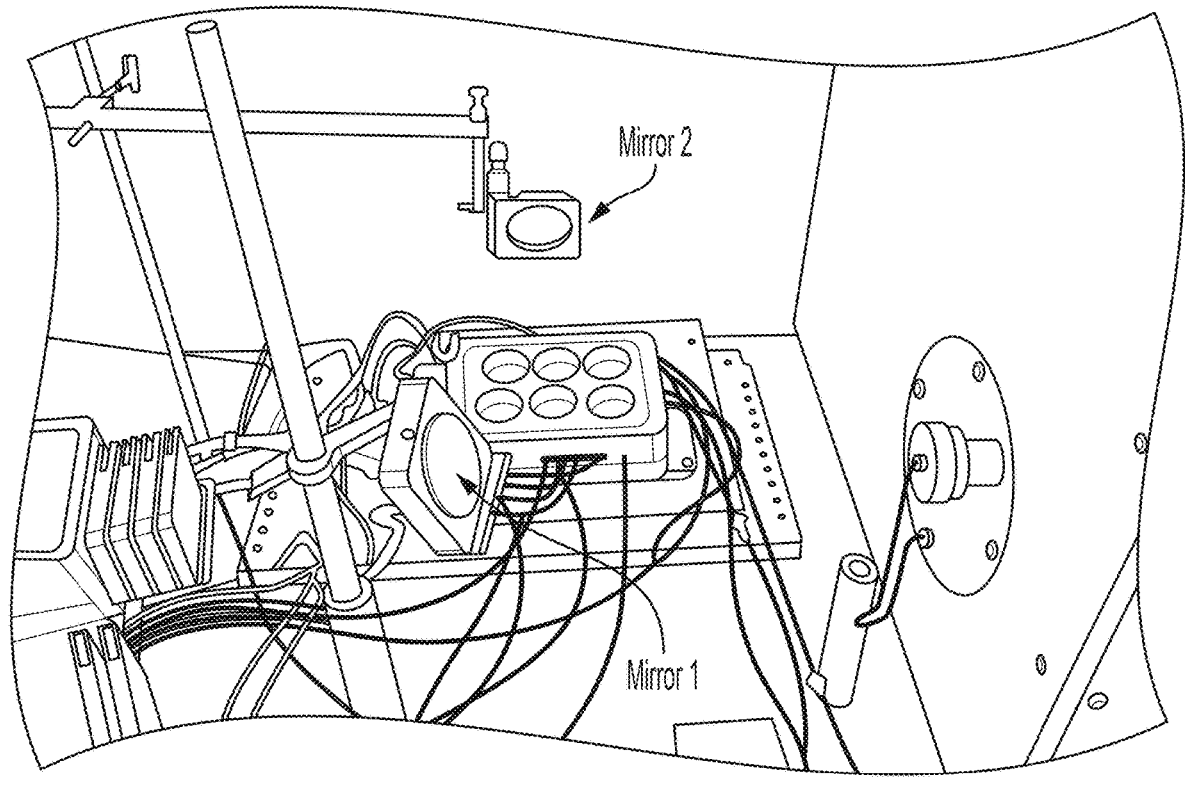
FIG. 11 is a photograph that shows a preferred configuration of lenses/mirrors for laser reflection downward onto the stage-top incubator, showing a preferred conformation of two mirrors to aim the laser (arrows).

In a different specific embodiment (see FIG. 11) the laser is aimed using two 50.0 mm 248 nm 45°, excimer laser line mirrors. Each mirror is made stationary, preferably by fastening to a post (for example by a PMTR-Component Clamp for $\emptyset\frac{1}{2}$" Posts, $\frac{1}{4}$"-20Taps). The stage is positioned towards the edge of the breadboard to accommodate movement. The first excimer line mirror is placed about 10.5 inches away from the laser source. This mirror is positioned to reflect the entire beam to the second mirror, located 9.5 inches away at an approximately 90 degree angle. The second mirror collects the entire beam and is angled downward at 45 degrees at a height of 3 inches, allowing full irradiation of one single well with one laser pulse. There is no scattering of the beam or loss of energy with this type of arrangement.

Using the software, the nanopositioning system can be programmed to move across each well as pictured in FIG. 3D or to move from well to well. In general, the first well is aligned with the laser beam, and the positioning system is either directed to move in a continuous manner in the XY plane so that the laser irradiates the entire well, and then to move to the start position for irradiation of the subsequent well, or directed to move to a first well for irradiation of the entire well and then to the position for irradiation of the subsequent wells in sequence. Precise alignment of each well in relation to the laser beam (or vice versa) should be used to ensure complete irradiation of each well. To confirm irradiation of the entire well, well irradiation can be visualized by placing a piece of white cardstock paper in the inside of the well. Laser irradiation burns an imprint the size of the laser beam on the paper. Preferably, the movement of the multi-well plate and/or the beam of the laser is automated.

Figure 3E:
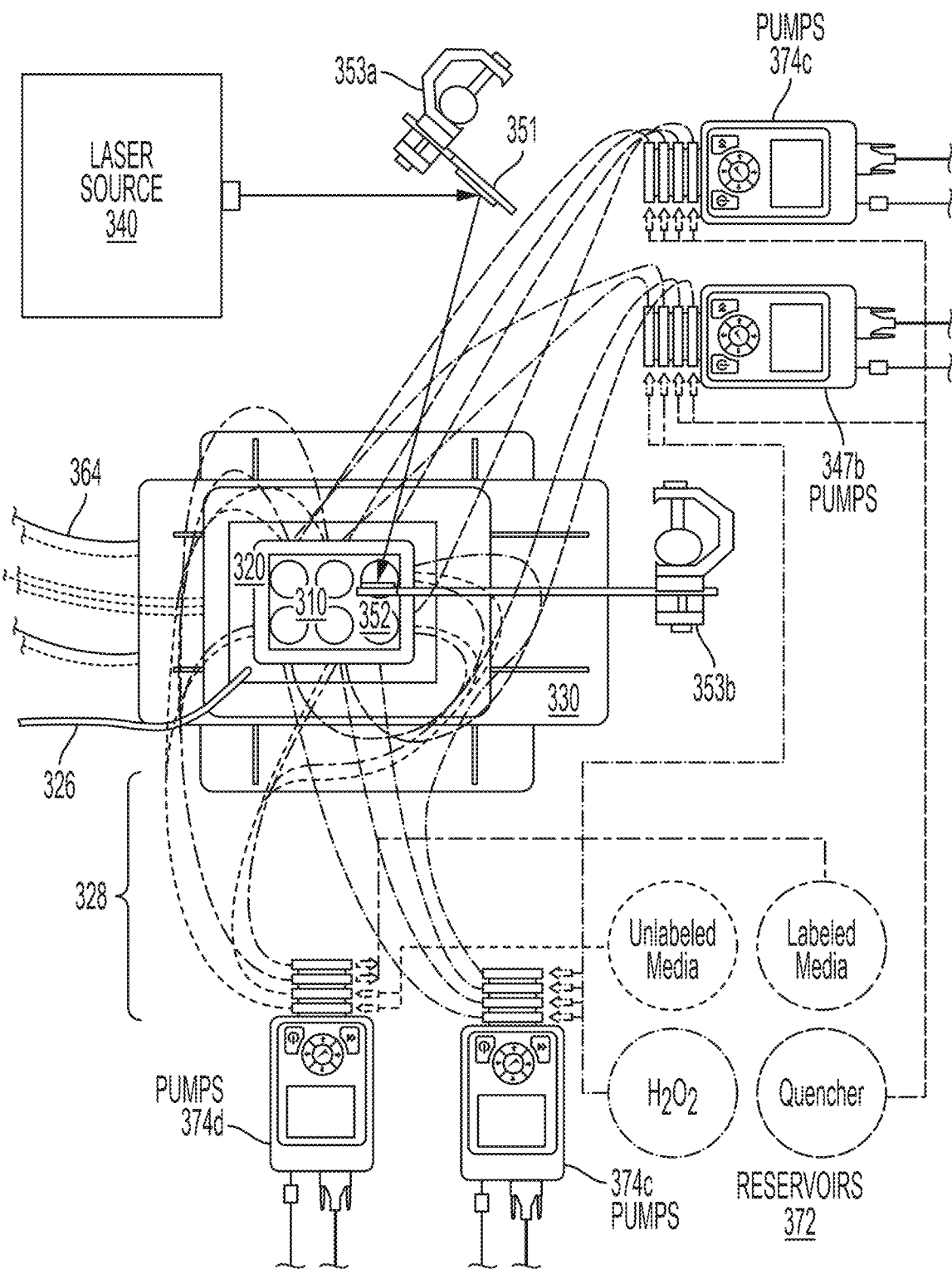

FIG. 3E is a block diagram that illustrates an example plan view of much of the system 100 using components described above with respect to FIG. 3A through FIG. 3D, according to an experimental embodiment. The stage 330 with at least two perpendicular stepping platforms cradle incubator 320 in which has been inserted a plate 310 with six wells. 312. Environmental supply and control lines 326 to incubator 320 are shown: as are control lines 364 to the motors (not shown) that drive the two perpendicularly moving platforms of stage 330.

Perfusion tubes 328 spread from distal ends over positions of individual wells through incubator 320 to proximal ends connected to pump assemblies 374a, 374b, 374c and 374d, each assembly controlling four individual infusion tube pumps, and thence to one of four reservoirs 372. For example, in some embodiments, 4 peristaltic pumps, each pump with 4 individual channels allows the control of infusion and withdrawal along 16 perfusion tubes. One perfusion tube from each of the six wells is connected through one or more infusion tube pumps to a reservoir of mass spectrometry label feeding media, as indicated by short-long dashed lines. A second, different, perfusion tube from each of the six wells is connected through one or more infusion tube pumps to a reservoir of unlabeled feeding media, as indicated by short dashed lines. A third, still different, perfusion tube from each of the six wells is connected through one or more infusion tube pumps to a reservoir of hydrogen peroxide, as indicated by dot-dashed lines. A fourth, yet different, perfusion tube from each of the six wells is connected through one or more infusion tube pumps to a reservoir of quenching fluid ("Quencher"), as indicated by long dashed lines.

Hydroxyl ions are produced when a well 312 is filled with hydrogen peroxide, by illuminating the well with a laser beam 342 from laser source 340 through mirrors 351 and 352, fixed to stands 353a and 353b, respectively. In an example embedment, the laser light is reflected downward onto the incubator. In some embodiments, each well is illuminated in sections, such as the 13 sections of well 312 depicted in FIG. 3D. In another embodiment, the whole well can be illuminated with one beam without significant loss of laser intensity using two excimer laser line mirrors that are 50 mm wide. The first mirror reflects the entire beam at an approximately 90° angle to the second mirror. The second mirror collects the entire beam and angles it downward at 45° allowing full irradiation of one single well.

Figure 3F:
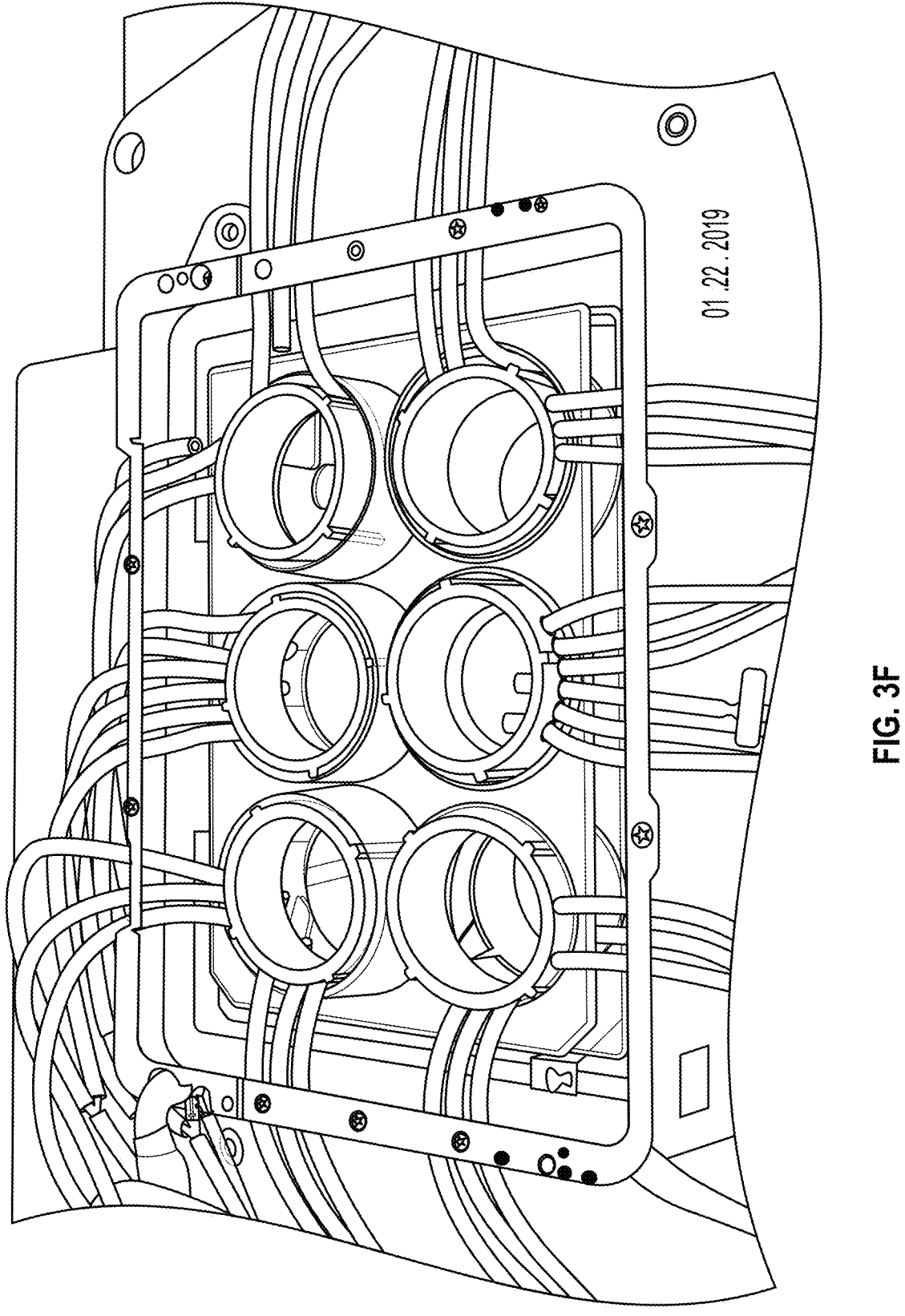
FIG. 3F is a photograph that illustrates an example incubator with at least 6 perfusion tubes leading to distal ends at each well position for a six well plate.

FIG. 3F is a photograph that illustrates an example incubator, according to an embodiment. One can clearly see at least 6 perfusion tubes leading to distal ends at each well position for a six well plate. Of these six perfusion lines, four are used according to the method of FIG. 4.

For fast analysis of multiple time points, the addition and removal of media, $H_2O_2$, and quench solution should be performed rapidly and reproducibly. Once the stage top incubator and the movement of the nanopositioning system have been coordinated, all of the parts of the system can be automated to achieve the fast and reproducible testing. Further, because the stage top incubator is a closed system, direct manual introduction of the various liquids into each well is not possible.

For automation of the pcIC-FPOP setup, all components are controlled individually by their respective software. The time frame of each condition is taken into account and each instrument is programmed to start at the respective time. The addition of $H_2O_2$ to each well is dependent on the chase time points to be studied. For testing the automation, chase time points of 1, 5, 10, 30, and 60 seconds can be tested, for example. The peristaltic pumps are initiated first to begin the pulse. All 4 pumps (16 channels) can be remotely controlled through software.

Upon the addition of $H_2O_2$ in well 1, the nanopositioning system aligns well 1 with the laser beam and begins to scan the well across the laser beam or remains stationary during irradiation of the entire well with one laser pulse. The timing of this system is coordinated so that movement to well 2 does not occur until $H_2O_2$ is added to well 2. The laser irradiation is initiated via a frequency generator that can send a pulse to the laser that immediately initiates laser irradiation. The frequency generator and thus timing of the laser pulse can be controlled remotely using the software. The laser pulse is stopped between time points to avoid any stray laser irradiation as the plate or the laser beam is moving. The laser control software also is programmed to stop the laser after the shot(s) required for irradiation of each well. It is standard for the laser control software to dictate the number of laser pulses required and to automatically shut off once the maximum number of pulses is reached. A second pulse from the frequency generator initiates the laser for well 2 and this continues until each well is irradiated. The frequency of the laser pulse is adjusted to correspond with its relative movement compared to the multi-well plate.

By automating each instrument, the need for user input once the peristaltic pumps are initiated is eliminated. The automation for each instrument can be tested using the time points above or any suitable time points. Other time points also can be tested to assess the automation. The software allows arbitrary timing between wells with a projected minimum of 50 milliseconds to about 650 milliseconds for the methods where scanning of the well (thirteen laser pulses are used to irradiate the entire well) is used, due to the time needed to move the nanopositioning system, and no upper limit, so that long, 10 second- to several-minute long chases as are used in traditional radioactive pulse-chase experiments can be used here. In this embodiment, chase points can be separated by about 50 milliseconds to about one hour, or longer. In the preferred embodiment, where mirrors are employed to enable only one laser pulse to irradiate the entire well, even shorter intervals between chase points can be achieved.

Temporal coordination of all of the instruments using their respective software is important to the ideal function of the apparatus and method. The various software communicate with one another or utilize systems engineering software that can communicate with the laser, optionally with the beam steering optics, nanopositioning system, and the peristaltic pumps.

The apparatus pictured in FIG. 3E produces cell cultures that contain proteins that are suitable for mass spectrometry analysis and are labeled with hydroxy groups on the areas of the protein that are accessible to the solvent, in the natural environment inside the cells. Cell lysates are produced from these cell cultures, and the lysates and other cellular fractions are analyzed by mass spectroscopy to produce spectra.

5. Example Method Embodiments

General pulse-chase methods are as follows. A multi-well plate is inoculated with cells expressing the protein to be studied and the cells are allowed to grow until confluence. In a cell culture hood, starving medium (medium lacking Arg and Lys) is added to all of the wells containing the cells expressing the protein of interest. The plate is transferred into a stage top incubator, the perfusion lines are placed in each well, and the stage top incubator then is placed in the nanopositioning system at the laser platform and connected to a temperature controller and $CO_2$ controller. After about 1 hour of incubation, "feeding" medium is added to all of the wells (the pulse) using a peristaltic pump. This medium contains all nutrients required by the cells for health during the period of study and a mass spectrometry label. Preferably, the medium contains $^{15}N$-arginine and $^{15}N$-lysine, but any convenient and stable isotopic label suitable for use with mass spectrometry of proteins, such as $^{15}N$-arginine, $^{15}N$-lysine or both, can be used. The feeding medium, in some embodiments, can be the same as the starving medium, with the addition of arginine and lysine, which in the pulse are isotopically enriched or labeled with $^{15}N$-arginine and $^{15}N$-lysine.

After a certain period of time (the time it takes for the label to be incorporated into newly synthesized proteins and to generate a detectable population of newly synthesized protein), the heavy labeled medium is removed and regular (unlabeled) feeding medium is added to each well at the same time. The length of the pulse, where the cells in each well are exposed to the $^{15}N$-labeled amino acids, prior to the first/initial chase point, can extend from less than one second to about 120 minutes, preferably from about 20 minutes to about 60 minutes, and most preferably from about 25 minutes to about 30 minutes, and is dependent on the protein system being studied. The person of skill can easily determine the length of time to pulse the cells depending on the type of cells being used by routine testing using traditional pulse-chase analysis.

At various time points after the pulse, $H_2O_2$ is added to an individual well (chase). That well, now referred to as well 1, then is subjected to laser irradiation (i.e. one second after the pulse, $H_2O_2$ is added to well 1) at about 238 nm to about 270 nm, preferably 248 nm, for a duration of about 1 nanosecond to about 50 nanoseconds, preferably 17 nanoseconds. A quench solution is added to well 1 immediately after laser irradiation. Thus, this first well is subjected to production of hydroxyl radicals for a known time period and the proteins become labeled with hydroxyl groups at the locations that were accessible to solvent at the time the hydroxyl radicals were present. Another well, here referred to as well 2 or the next well is subjected to the same treatment of $H_2O_2$ pulse, laser irradiation, and quenching at a set time point after well 1 is pulsed with $H_2O_2$. This continues to well 3, well 4, and so on, until all wells in the multi-well plate are treated to $H_2O_2$ pulse, laser irradiation, and quenching at different times after the $^{15}N$-arginine and $^{15}N$-lysine pulse. Thus, succeeding wells also contain proteins that have been labeled by added hydroxyl groups at the locations that were accessible to solvent at the time the hydroxyl radicals were present, each successive sample representing a different time after the pulse occurred. The optimal times used for the pulse and chase points depend on the individual cells and proteins, and the time frame that the investigator would like to capture to study the folding of a particular protein. After the sequence of chases have been completed, with all wells quenched, samples are taken of cell lysates, which are analyzed by mass spectrometry, optionally with a prior purification step.

Although preliminary results indicate that Huh-7 cells begin to incorporate labeled Arg and Lys at times as short as 1 minute, this time may not be sufficient to generate a detectable population of A1AT. For gel electrophoresis studies with $^{35}$S labeled cysteine, pulse times as long as 20 minutes to one hour were used to generate a detectable population of protein. In eukaryotes, translation occurs at a rate of about 6 amino acids per second. For A1AT, which, with the signal peptide sequence is 418 amino acids long, it would take about 70 seconds to synthesize a single chain of the protein. A single chain of protein may not be detectable by mass spectrometry, so the pulse times for pcIC-FPOP preferably should be optimized to avoid wasting time and reagent. For this, several pulse times can be tested to determine when a detectable amount of newly synthesized A1AT, or another protein is achieved in a certain cell type, whether the cells naturally express the protein or the cells are manipulated to transiently express the protein. The minimum pulse time is about 20 minutes based on the data in Example 4 (see FIG. 12A). Several times points including 25, 30, 35, 40, and 60 minutes also can be tested to determine the best pulse time. Because Huh-7 cells continuously synthesize A1AT, longer pulse times to generate a detectable population would not limit the ability to study A1AT folding.

In order to obtain a complete view of the folding pathway of A1AT or any other protein, the chase time points should be chosen so as to be sufficient to observe intermediates in protein production in the cell. To optimize chase time points, and based on the data in FIG. 12A, the chase time points preferably are several minutes apart. The same time points preferably are tested first, then, shorter chase time points also can be evaluated to determine whether any short-lived intermediates can be detected early in the folding pathway that are not detected with the initial, longer chase time points.

IC-FPOP has been performed on Vero cells, kidney cells from the African green monkey, where 20 mM $H_2O_2$ is sufficient to oxidatively modify 1391 proteins within various compartments in the cell. At this concentration, cell viability assays determine that >70% of cells were metabolically active after peroxide exposure. However, owing to cell line variability, 20 mM $H_2O_2$ may be excessive or not sufficient to modify proteins within Huh-7 cells. To determine the best $H_2O_2$ concentration for oxidatively modifying a protein, for example A1AT in Huh-7 cells, various concentrations including 10, 20, 40, 50, 80, 100, 150, and 200 mM can be tested. In addition to testing the oxidative coverage of A1AT by mass spectrometry, a cell viability assay is performed to determine the metabolic effect of each $H_2O_2$ concentration. The concentration with the best oxidation coverage of A1AT where >70% of cells are still viable is suitable for further pcIC-FPOP studies.

The initial chase point (exposure to $H_2O_2$ and laser irradiation of well 1) can begin immediately, or a few seconds after the pulse, or after several minutes. For example, the initial chase point can occur immediately or from about less than one second to about 10 minutes, preferably to about 60 seconds and most preferably to about 15 seconds, and continue to the next wells at regular or irregular intervals between the chase points of about 500 milliseconds, 1 second, 2 seconds, 4 seconds, 5 seconds, or more, including about 15 seconds, about 30 seconds, about 60 seconds or any time interval which is convenient to the operator. The timing and duration of both the pulse and chase times preferably are optimized for each different cell/protein system to be tested. See Examples, below, and the discussion above.

$H_2O_2$ is added to each well to achieve a concentration of about 50 mM to about 500 mM, preferably about 100 mM to about 200 mM, and most preferably about 100 mM, including 10 mM, 20 mM, 40 mM, 50 mM, 80 mM, 100 mM, 150 mM, and 200 mM. The person of skill is expected to modify the concentration to achieve sufficient hydroxyl radicals to produce detectable labeling, while avoiding over exposure of the cells to $H_2O_2$ which could harm the cells and lead to erroneous results. In general, concentrations above about 20 mM are sufficient to produce good levels of labeling, while concentrations below about 500 mM are low enough to avoid over-reaction.

Quencher solutions for use in the invention depend on the reaction being used. In certain embodiments, where $H_2O_2$ is used, the quencher compound is a mixture of N-tert-butyl-α-phenylnitrone (PBN) and dimethylthiourea (DMTU), which is added to produce a concentration of about 100 mM to about 200 mM PBN and about 100 mM to about 200 mM DMTU, preferably about 120 mM to about 150 mM PBM and about 120 mM to about 150 mM DMTU, or most preferably at about 120 mM to about 125 mM PBN and about 120 mM to about 125 mM DMTU, for example about 125 mM. Other quenchers that can be used include DMSO and the nitrone spin traps DMPO and 4-POBN.

After the chase point exposures to hydroxyl radicals have been completed, cell lysates of each well are assayed by MS. Prior to MS, the cell lysates optionally are purified or semi-purified. Oxidative modification of proteins in interacting sites generally decreases their affinity for their binding partners including antibodies. Therefore, affinity purification to isolate the protein prior to MS analysis may not be feasible by this method. To obtain high sequence coverage of a protein such as A1AT by MS, alternate strategies can be used. Coupling FPOP of cell lysates with Multidimensional Protein Identification (MudPIT), an on-line 2-dimensional liquid chromatography method, increased the identification of unique oxidatively modified proteins by 2.7-fold. Coupling pcIC-FPOP with 2-D chromatography also can lead to increased sequence coverage. LC-MS/MS analysis can be performed on either a Thermo Scientific Fusion Orbitrap™ or a Q-Exactive Orbitrap™. Any purification protocol that is convenient can be used as convenient, for example any of the methods used by those of skill in the art.

Cells which are suitable for use with the invention include any convenient primary cells or cell lines that express the protein of interest, preferably in large amounts. In certain embodiments, the cells are recombinant cells that have been manipulated to express or overexpress the protein of interest. Exemplary cells include but are not limited to Huh-7 cells, Chinese Hamster Ovary cells, HEK cells, and HeLa cells. Preferred cells in certain embodiments include Huh-7 cells. Any protein can be studied as well, included secreted proteins and membrane proteins, or any protein of interest in the study of disease, for example superoxide dismutase 1 and other proteins associated with ALS. The cells are maintained under culture conditions as known in the art for whatever cells are chosen.

Due to the many possible modifications that can occur on the side chains of amino acids when exposed to hydroxyl radicals, data analysis is a major challenge that is often time consuming. A multi-level strategy to decrease analysis time was developed using multiple filters to yield high confidence MS/MS data. This strategy can be used to identify oxidatively modified proteins with one change. In the first stage of searching in this test, only $^{15}$N-labeled peptides containing [15]N-Lys or [15]N-Arg (A1AT contains 7 Arg residues and 34 Lys residues spread throughout the sequence) are looked for (since only newly synthesized proteins are of interest) rather than using a strategy where unmodified peptides are searched in the first stage. Software was specifically used to quantitate modifications on proteins and is beginning to be used for FPOP data analysis. After database searching, software is used for the quantitation of FPOP modification on A1AT. Because there is a wealth of data on the folding pathway of A1AT including in vitro FPOP, in-cell pulse-chase experiments and simulations, pcIC-FPOP data can be analyzed and compared to previous folding data to confirm that the method successfully reveals the folding of the protein. Since information is known on which regions of A1AT fold first, this information can be used to confirm that pcIC-FPOP has utility in studying protein folding pathways.

To fully investigate protein folding pathways, it is beneficial to have structural information on chaperones that interact with proteins as they fold. Therefore, the inventive method also can be used to study the effects of chaperone proteins that interact with A1AT during folding. Upon removal of glucose from the co-translational glycan, the lectin chaperones calnexin or calreticulin can bind the glycan on the nascent chain. Chaperone binding leads to recruitment of ERp57, an accessory oxidoreductase involved in disulfide bond formation and isomerization. The role of chaperone binding is not to aid in the folding of proteins; rather the chaperones help control the rate of the folding process and minimize disruptive interactions that could lead to aggregate formation. pcIC-FPOP can be used to further investigate how these proteins interact with A1AT in the ER.

As there are multiple proteins being synthesized in the ER at a time, some calnexin proteins may be interacting with one protein while other copies of calnexin may be interacting with another protein. For traditional in-cell studies, immunoprecipitation would be used to pull down the protein of interest with interaction proteins bound. As mentioned previously, this might not be possible with pcIC-FPOP so other means can be used. In order to distinguish the chaperones, isomerases, and other proteins that are specifically interacting with A1AT, photoreactive cross-linkers can be used.

Mass spectrometry (MS) is an analytical technique that sorts different chemicals after ionization, based on their mass-to-charge ratio to determine the masses of chemicals within a sample, including complex mixtures. In a typical MS procedure, a sample is ionized by bombardment with electrons, which can break some of the molecules in the sample into charged fragments. These ions are separated according to their mass-to-charge ratio and detected by an electron multiplier. Results of MS are presented as a graph of the ion signal as a function of the mass-to-charge ratio, or "spectra" of the relative abundance of detected ions as a function of the mass-to-charge ratio. These are used to determine the elemental or isotopic signature of a sample, the masses of particles and of molecules, and their chemical structure. The atoms or molecules in the sample can be identified by correlating known masses (e.g. an entire molecule) to the identified masses or through a characteristic fragmentation pattern. Data are prepared according to the methods of Espino et al., Anal. Chem. 87:7971-7978, 2015 and Rinas et al., Anal. Chem. 88:10052-10058, 2016. A standard proteomics workflow preferably is used for LC-MS/MS analysis (for example, according to Zhang et al., Chem. Rev. 113:2343-2394, 2013) and data interpretation preferably is performed according to known methods (for example, according to Rinas et al., Anal. Bioanal. Chem. 408:3021-3031, 2016.

26

6. Computational Hardware Overview

Figure 5:
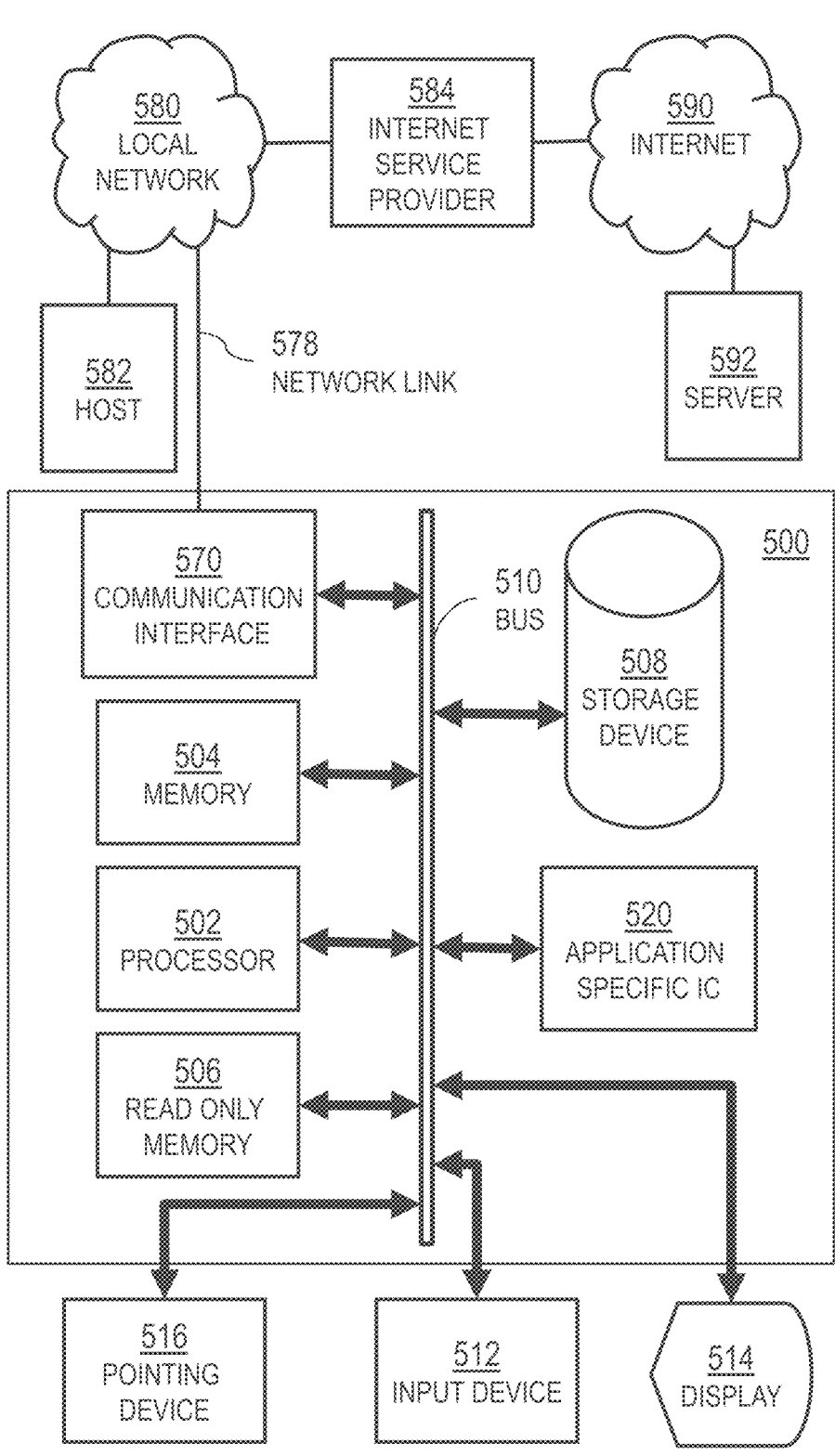
FIG. 5 is a block diagram that illustrates a computer system upon which an embodiment of the invention may be implemented.

FIG. 5 is a block diagram that illustrates a computer system 500 upon which an embodiment of the invention may be implemented. Computer system 500 includes a communication mechanism such as a bus 510 for passing information between other internal and external components of the computer system 500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 500, or a portion thereof, constitutes a means for performing one or more steps of one or more methods described herein.

A sequence of binary digits constitutes digital data that is used to represent a number or code for a character. A bus 510 includes many parallel conductors of information so that information is transferred quickly among devices coupled to the bus 510. One or more processors 502 for processing information are coupled with the bus 510. A processor 502 performs a set of operations on information. The set of operations include bringing information in from the bus 510 and placing information on the bus 510. The set of operations also typically include comparing two or more units of information, shifting positions of units of information, and combining two or more units of information, such as by addition or multiplication. A sequence of operations to be executed by the processor 502 constitutes computer instructions.

Computer system 500 also includes a memory 504 coupled to bus 510. The memory 504, such as a random access memory (RAM) or other dynamic storage device, stores information including computer instructions. Dynamic memory allows information stored therein to be changed by the computer system 500. RAM allows a unit of information stored at a location called a memory address to be stored and retrieved independently of information at neighboring addresses. The memory 504 is also used by the processor 502 to store temporary values during execution of computer instructions. The computer system 500 also includes a read only memory (ROM) 506 or other static storage device coupled to the bus 510 for storing static information, including instructions, that is not changed by the computer system 500. Also coupled to bus 510 is a non-volatile (persistent) storage device 508, such as a magnetic disk or optical disk, for storing information, including instructions, that persists even when the computer system 500 is turned off or otherwise loses power.

Information, including instructions, is provided to the bus 510 for use by the processor from an external input device 512, such as a keyboard containing alphanumeric keys operated by a human user, or a sensor. A sensor detects conditions in its vicinity and transforms those detections into signals compatible with the signals used to represent information in computer system 500. Other external devices coupled to bus 510, used primarily for interacting with humans, include a display device 514, such as a cathode ray tube (CRT) or a liquid crystal display (LCD), for presenting images, and a pointing device 516, such as a mouse or a trackball or cursor direction keys, for controlling a position of a small cursor image presented on the display 514 and issuing commands associated with graphical elements presented on the display 514.

In the illustrated embodiment, special purpose hardware, such as an application specific integrated circuit (IC) 520, is coupled to bus 510. The special purpose hardware is configured to perform operations not performed by processor 502 quickly enough for special purposes. Examples of application specific ICs include graphics accelerator cards for generating images for display 514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 500 also includes one or more instances of a communications interface 570 coupled to bus 510. Communication interface 570 provides a two-way communication coupling to a variety of external devices that operate with their own processors, such as printers, scanners, and external disks. In general, the coupling is with a network link 578 that is connected to a local network 580 to which a variety of external devices with their own processors are connected. For example, communication interface 570 may be a parallel port or a serial port or a universal serial bus (USB) port on a personal computer. In some embodiments, communications interface 570 is an integrated services digital network (ISDN) card or a digital subscriber line (DSL) card or a telephone modem that provides an information communication connection to a corresponding type of telephone line. In some embodiments, a communication interface 570 is a cable modem that converts signals on bus 510 into signals for a communication connection over a coaxial cable or into optical signals for a communication connection over a fiber optic cable. As another example, communications interface 570 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 570 sends and receives electrical, acoustic or electromagnetic signals, including infrared and optical signals, that carry information streams, such as digital data.

The term computer-readable medium is used herein to refer to any medium that participates in providing information to processor 502, including instructions for execution. Such a medium may take many forms, including, but not limited to, non-volatile media, volatile media and transmission media. Non-volatile media include, for example, optical or magnetic disks, such as storage device 508. Volatile media include, for example, dynamic memory 504. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 502, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 502, except for carrier waves and other signals.

Logic encoded in one or more tangible media includes one or both of processor instructions on a computer-readable storage media and special purpose hardware, such as ASIC *920.

Network link 578 typically provides information communication through one or more networks to other devices that use or process the information. For example, network link 578 may provide a connection through local network 580 to a host computer 582 or to equipment 584 operated by an Internet Service Provider (ISP). ISP equipment 584 in turn provides data communication services through the public, world-wide packet-switching communication network of networks now commonly referred to as the Internet 590. A computer called a server 592 connected to the Internet provides a service in response to information received over the Internet. For example, server 592 provides information representing video data for presentation at display 514.

The invention is related to the use of computer system 500 for implementing the techniques described herein. According to one embodiment of the invention, those techniques are performed by computer system 500 in response to processor 502 executing one or more sequences of one or more instructions contained in memory 504. Such instructions, also called software and program code, may be read into memory 504 from another computer-readable medium such as storage device 508. Execution of the sequences of instructions contained in memory 504 causes processor 502 to perform the method steps described herein. In alternative embodiments, hardware, such as application specific integrated circuit 520, may be used in place of or in combination with software to implement the invention. Thus, embodiments of the invention are not limited to any specific combination of hardware and software.

The signals transmitted over network link 578 and other networks through communications interface 570, carry information to and from computer system 500. Computer system 500 can send and receive information, including program code, through the networks 580, 590 among others, through network link 578 and communications interface 570. In an example using the Internet 590, a server 592 transmits program code for a particular application, requested by a message sent from computer 500, through Internet 590, ISP equipment 584, local network 580 and communications interface 570. The received code may be executed by processor 502 as it is received, or may be stored in storage device 508 or other non-volatile storage for later execution, or both. In this manner, computer system 500 may obtain application program code in the form of a signal on a carrier wave.

Various forms of computer readable media may be involved in carrying one or more sequence of instructions or data or both to processor 502 for execution. For example, instructions and data may initially be carried on a magnetic disk of a remote computer such as host 582. The remote computer loads the instructions and data into its dynamic memory and sends the instructions and data over a telephone line using a modem. A modem local to the computer system 500 receives the instructions and data on a telephone line and uses an infra-red transmitter to convert the instructions and data to a signal on an infra-red a carrier wave serving as the network link 578. An infrared detector serving as communications interface 570 receives the instructions and data carried in the infrared signal and places information representing the instructions and data onto bus 510. Bus 510 carries the information to memory 504 from which processor 502 retrieves and executes the instructions using some of the data sent with the instructions. The instructions and data received in memory 504 may optionally be stored on storage device 508, either before or after execution by the processor 502.

Figure 6:
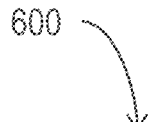
FIG. 6 illustrates a chip set upon which an embodiment of the invention may be implemented.
Figure 6:
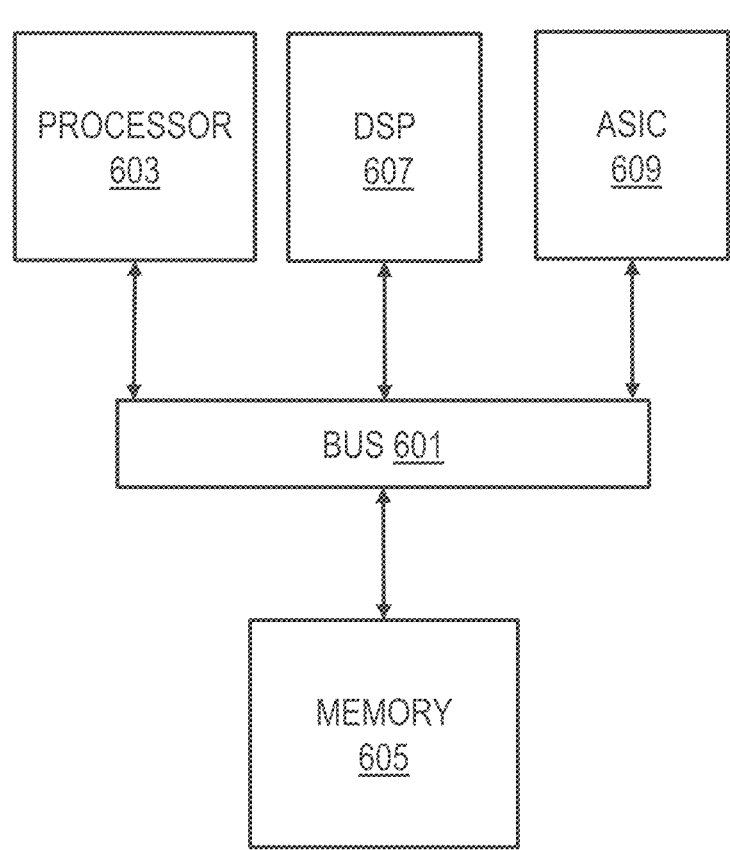

FIG. 6 illustrates a chip set 600 upon which an embodiment of the invention may be implemented. Chip set 600 is programmed to perform one or more steps of a method described herein and includes, for instance, the processor and memory components described with respect to FIG. 5 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 600, or a portion thereof, constitutes a means for performing one or more steps of a method described herein.

In one embodiment, the chip set 600 includes a communication mechanism such as a bus 601 for passing information among the components of the chip set 600. A processor 603 has connectivity to the bus 601 to execute instructions and process information stored in, for example, a memory 605. The processor 603 may include one or more processing cores with each core configured to perform independently. A multi-core processor enables multiprocessing within a single physical package. Examples of a multi-core processor include two, four, eight, or greater numbers of processing cores. Alternatively, or in addition, the processor 603 may include one or more microprocessors configured in tandem via the bus 601 to enable independent execution of instructions, pipelining, and multithreading. The processor 603 may also be accompanied with one or more specialized components to perform certain processing functions and tasks such as one or more digital signal processors (DSP) 607, or one or more application-specific integrated circuits (ASIC) 609. A DSP 607 typically is configured to process real-world signals (e.g., sound) in real time independently of the processor 603. Similarly, an ASIC 609 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 603 and accompanying components have connectivity to the memory 605 via the bus 601. The memory 605 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 605 also stores the data associated with or generated by the execution of one or more steps of the methods described herein.

7. Alternatives, Deviations and Modifications

In the foregoing specification, the invention has been described with reference to specific embodiments thereof. It is, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," is understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

EXAMPLE PERFORMANCE

Example 1. Protein Footprinting Coupled with Mass Spectrometry

Figure 7B:
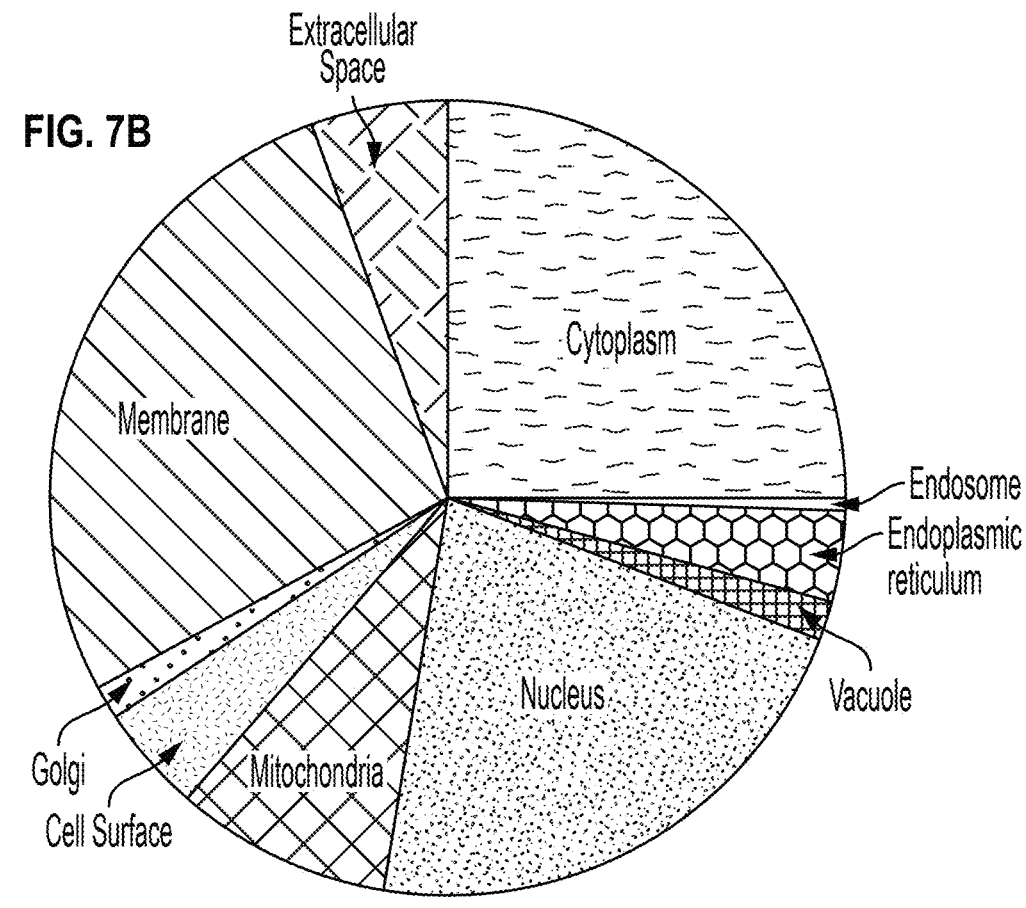
FIG. 7B is a pie chart showing cell compartments in which proteins can be modified.

FPOP has been extended here to in-cell protein folding studies. Initially, cell density, hydrogen peroxide concentration, quench conditions, and laser pulse rate were optimized, 105 proteins were oxidatively modified within various cellular organelles. To increase the number of proteins modified within the cell, a single cell flow system that is compatible with the laser and allows the cells to flow in a single file providing equal access to the laser light was developed and built (see FIG. 7A). Using this flow system, IC-FPOP was able to oxidatively modify over 1300 proteins within the cell, a 13-fold increase over the number of proteins modified without the flow system. Further, IC-FPOP was able to modify proteins in several different organelles in the cell including the nucleus and mitochondria (see FIG. 7B).

Figure 7C:
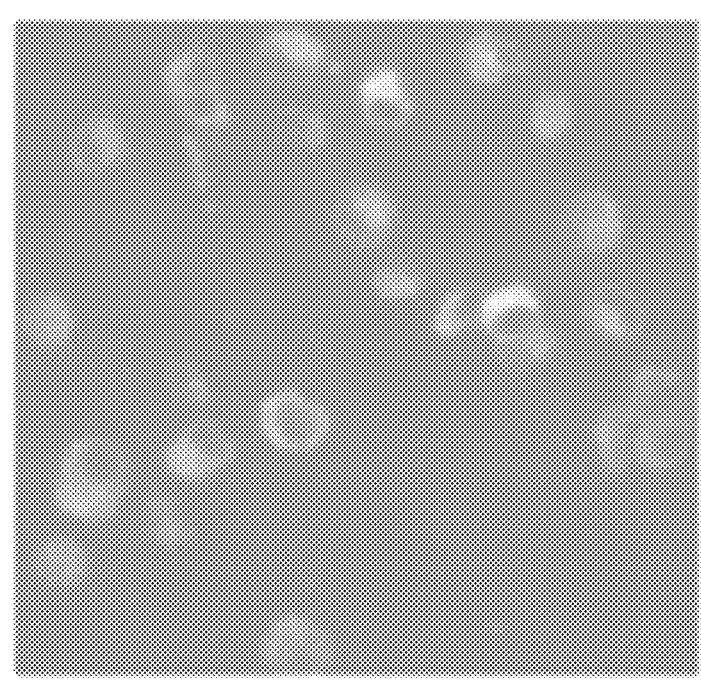
FIG. 7C is a photograph of fluorescence showing intact cells after IC-FPOP.
Figure 7D:
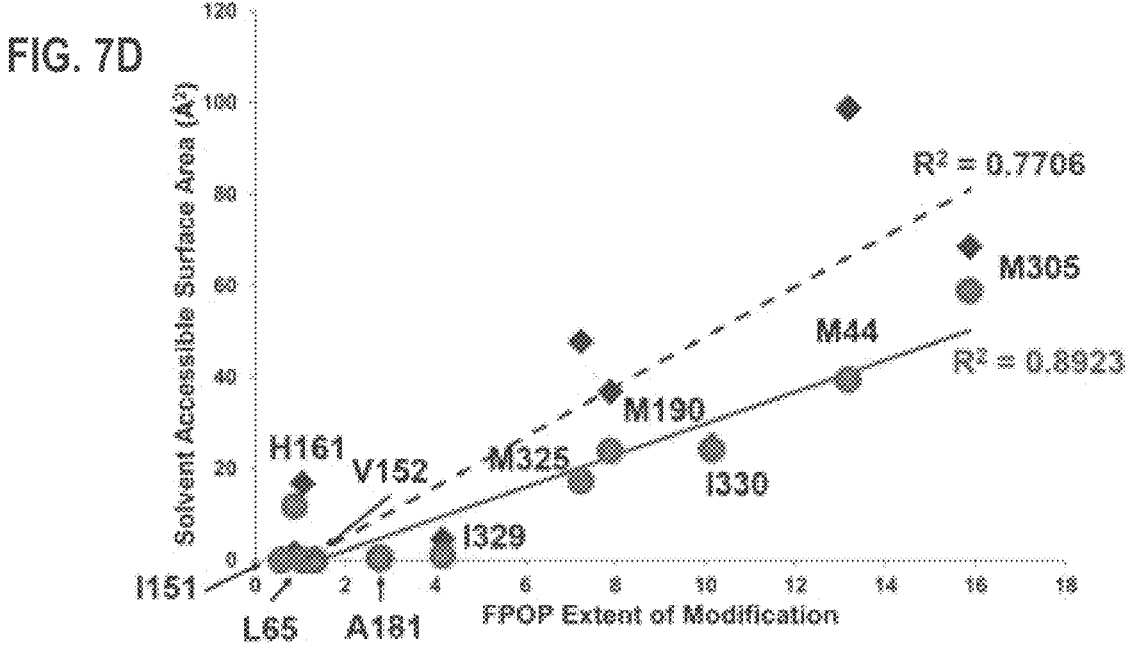
FIG. 7D is a graph showing the correlation of SASA calculated for the actin crystal structures 2BTF (triangles) and 1HLU (circles) with residue-level IC-FPOP data.

To ensure that IC-FPOP is modifying proteins in their native cellular environment and the laser is not disrupting the integrity of the cell, fluorescence imaging was used to analyze the cells after IC-FPOP. FIG. 7C shows that cells are intact after laser irradiation, indicating that IC-FPOP can label proteins in their native cellular environment regardless of what organelle they are located within and opens the door to studying a wide variety of protein systems. By correlating the residue-level oxidation levels of the protein actin modified by IC-FPOP to the solvent accessible surface area (SASA) calculated from the X-ray crystal structure of actin, the data also shows that IC-FPOP probes' solvent accessibility within the cell is similar to in vitro FPOP (FIG. 4D). This further demonstrates the efficacy of the method for analysis of protein structure within cells. The results described above and in the following examples demonstrate the feasibility of the apparatus and method.

Example 2. Test Cell Cultures

HEK293 cells were transiently transfected with GCaMP2 as a model system for testing the stage-top incubator for the ability to maintain cells under testing conditions. The cells were transfected using Lipofectamine according to the manufacturer's protocol. The cells then were plated in wells which were placed in the stage-top incubator.

The cells were incubated for 2 days at 37° C. and 5% $CO_2$, in wells in the stage-top incubator. Two days after transfection, the cells were imaged to detect GCaMP2 fluorescence.

Figure 8:
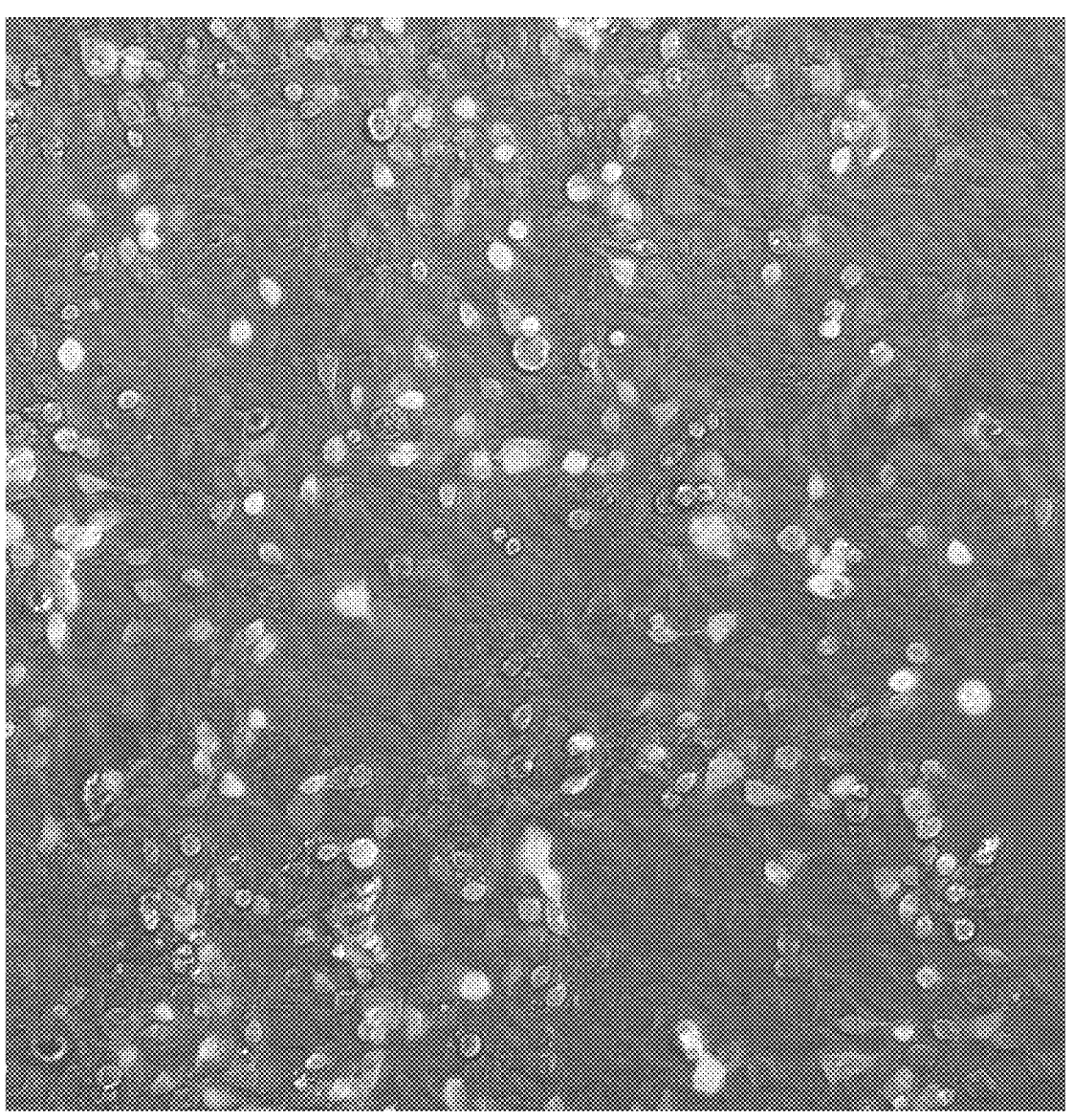
FIG. 8 is a photomicrograph showing fluorescence imaging of HEK293 cells transfected with GCamP2.

See FIG. 8. Significant GCaMP2 fluorescence was observed via fluorescence imaging. The transfection efficiency was about 50% (see FIG. 8). This test shows that the transiently transfected cells maintained in the stage-top incubator are suitable for testing by pcIC-FPOP.

In order to provide a quantitative benchmark for preservation of cellular function during incubation in the stage-top incubator, transient transfections of GCaMP2 in HEK 293 cells are performed in two 6-well plates using Lipofectamine 3000. One well plate is incubated in the stage top incubator and the second well plate is incubated in a standard $CO_2$ incubator. Two days after transfection, fluorescence imaging is performed on both plates for comparison of transfection efficiency.

Example 3. System Optimization for pcIC-FPOP

Figure 9:
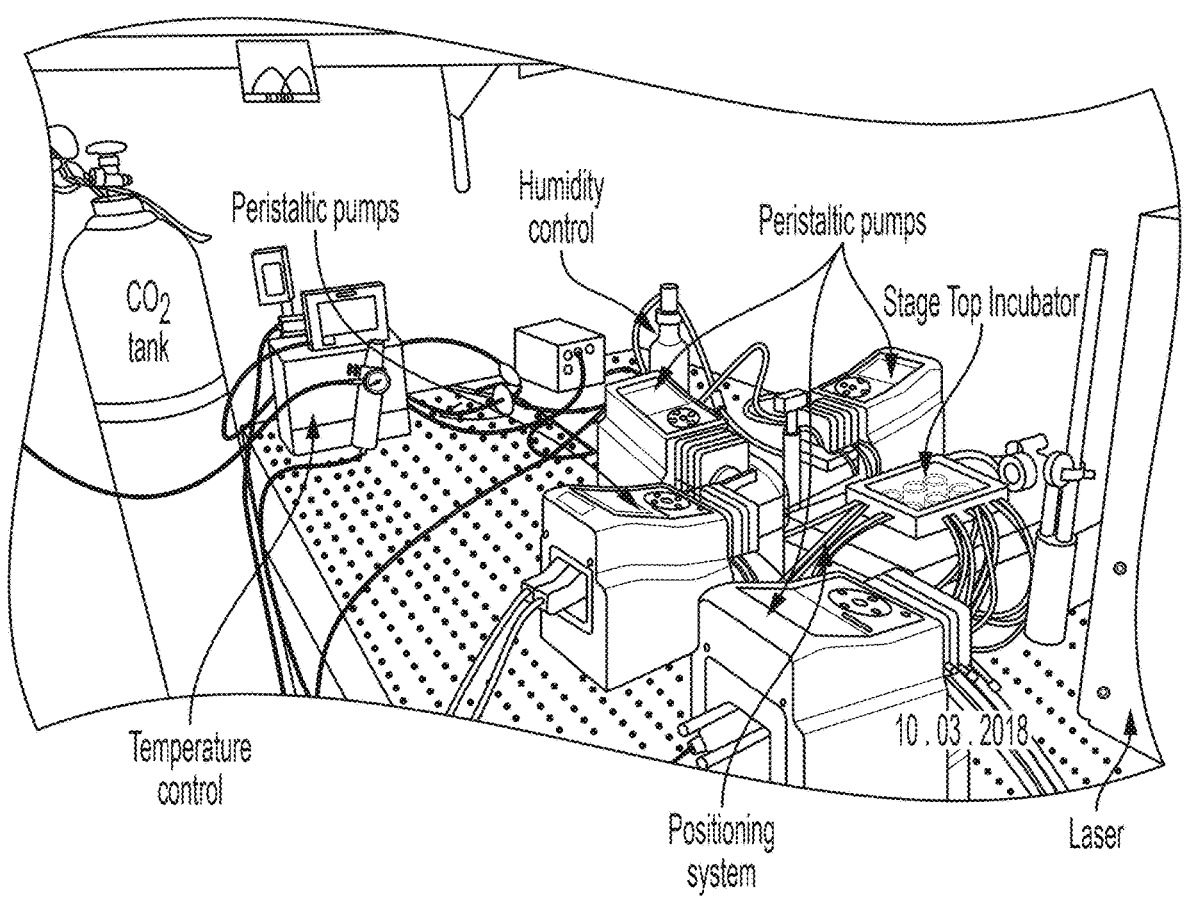
FIG. 9 is a photograph of an assembled system with laser, stage-top incubator, peristaltic pumps, CO2 input, and temperature control.

The inventive platform includes a stage top incubator which was fabricated by Okolab™ designed to perform the methods described here and a positioning system which was fabricated by Mad City Labs™ for cell culture at the laser. The system is assembled as shown in FIG. 9. The stage top incubator is completely enclosed and preferably kept at 37° C. with 5% $CO_2$. The platform also includes 4 peristaltic pumps. Each pump has 4 individual channels which can infuse and withdraw solutions independently of one another for a total of 16 flow channels.

Figure 10C:
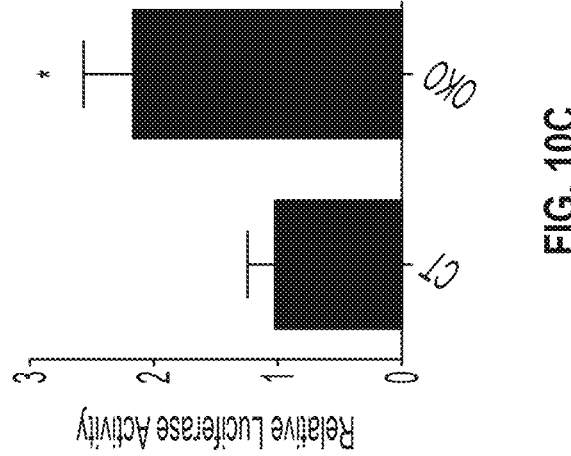
FIG. 10C is a bar graph showing the transfection efficiency of cells cultured in a standard incubator (CT) and in inventive incubator (OKO).
Figure 10B:
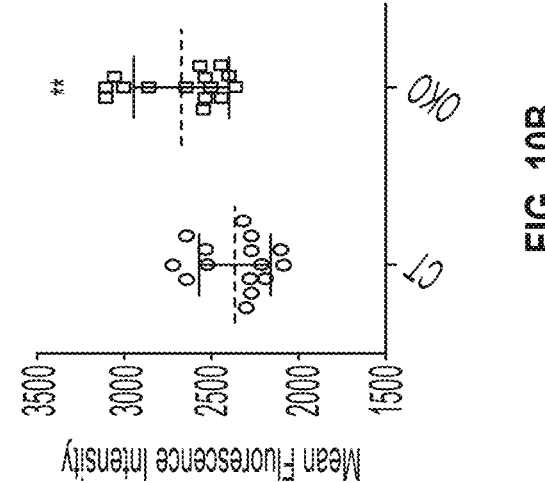
FIG. 10B is a graph showing the mean fluorescence intensity of GCamP2-transfected HEK cells in a standard incubator (CT) and in inventive incubator (OKO).
Figure 10A:
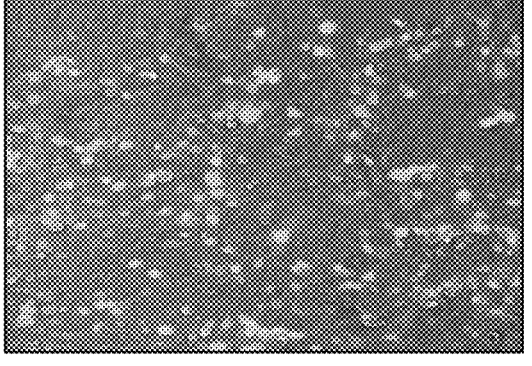
FIG. 10A is an image of fluorescence of HEK cells expressing GCamP2 in the inventive stage-top incubator.

To test the system, the transfection efficiency of the fluorescent protein GCamP2 was compared between the inventive stage-top incubator and a standard cell culture incubator. For this, GCamP2, a chimera of GFP and calmodulin, was transfected in HEK cells cultured in both incubators. Fluorescence imaging demonstrated that GCamP2 is expressed in cells cultured in the inventive incubator (see FIG. 10A). A comparison of the fluorescent intensity of GCamP2 in the inventive stage-top incubator (OKO) versus the standard incubator (CT) shows the fluorescence is higher in the inventive incubator (OKO) indicating the protein is being expressed in higher abundance there (see FIG. 10B). To quantitate this, a luciferase assay was performed to measure transfection efficiency. The transfection efficiency of GCamP2 was statistically significantly higher in the inventive incubator system than in the standard incubator (see FIG. 10C). Taken together, these data indicate the cells are biologically active in the stage top incubator and we can successfully perform cell culture at the laser platform.

Next, whether IC-FPOP could be performed in the stage top incubator was tested. For this, the laser light had to be reflected onto the incubator. Multiple lens and mirror configurations were tested to determine which had minimal laser energy loss. A loss in laser energy would correlate to a lower number of proteins being oxidatively modified by FPOP so it is highly preferred to use a configuration that results in the lease loss of laser energy. In a preferred embodiment, two excimer laser line mirrors that are 50 mm wide were used (see FIG. 11). The first mirror reflects the entire beam at an approximately 90° angle to the second mirror. The second mirror collects the entire beam and angles it downward at 45° allowing full irradiation of one single well. With this configuration there was no scattering of the beam or loss of energy. Owing to this, the two-mirror configuration was chosen for subsequent IC-FPOP experiments.

To determine whether oxidative modification of proteins could be achieved in the stage top incubator, IC-FPOP was performed on HEK cells using the inventive platform with the two-mirror configuration. In parallel, IC-FPOP was performed on HEK cells using a single cell flow system. A comparison of the number of oxidatively modified proteins indicated that both methods modify a comparable number of proteins, indicating that IC-FPOP can be performed in the inventive system without sacrificing the number of oxidatively modified proteins.

To be able to perform IC-FPOP on all wells in the plate on a second to minutes time scale, the entire inventive platform was automated using software which allows users to write their own code to automate instrumentation and have various instruments communicate with one another. This method was used here to write code to control the positioning system, each individual pump channel, and the laser, in one software module. A script builder allows for the control of each channel on a pump individually. The sequence builder allows for input of each part of the platform and their timing (e.g. laser pulse start), therefore it can be used to run the entire sequence of an experiment. The complete automation of the platforms allows for fast FPOP labeling on multiple wells and is useful in studying short-lived folding intermediates.

Example 4. $\alpha_1$-Antitrypsin as a Model System for pcIC-FPOP

A1AT is an abundant secretory protein that folds in the endoplasmic reticulum (ER). In order to monitor the folding of this protein, pcIC-FPOP has to oxidatively modify proteins in the ER. Previous IC-FPOP studies show that proteins that are found exclusively in the ER are modified. These include the molecular chaperone hypoxia up-regulated protein 1, an enzyme that catalyzes the formation and breakage of disulfide bonds, protein disulfide-isomerase A4, and the glycoprotein endoplasmin. These three proteins exclusively reside in the ER lumen. Additionally, ER membrane proteins dolichyl-diphosphooligosaccharide-protein glycosyltransferase subunit 2 and the molecular chaperone calnexin were also oxidized by IC-FPOP. These data demonstrate that IC-FPOP can oxidatively modify proteins in the ER so pcIC-FPOP can monitor the folding of A1AT. Additionally, hydrogen deuterium exchange MS experiments of the 1-190 fragment of A1AT demonstrate that footprinting can detect differences in folding between fragments and the full-length protein. This demonstrates the feasibility of using pcIC-FPOP to study protein folding as proteins are being synthesized in the cell.

Figure 12A:
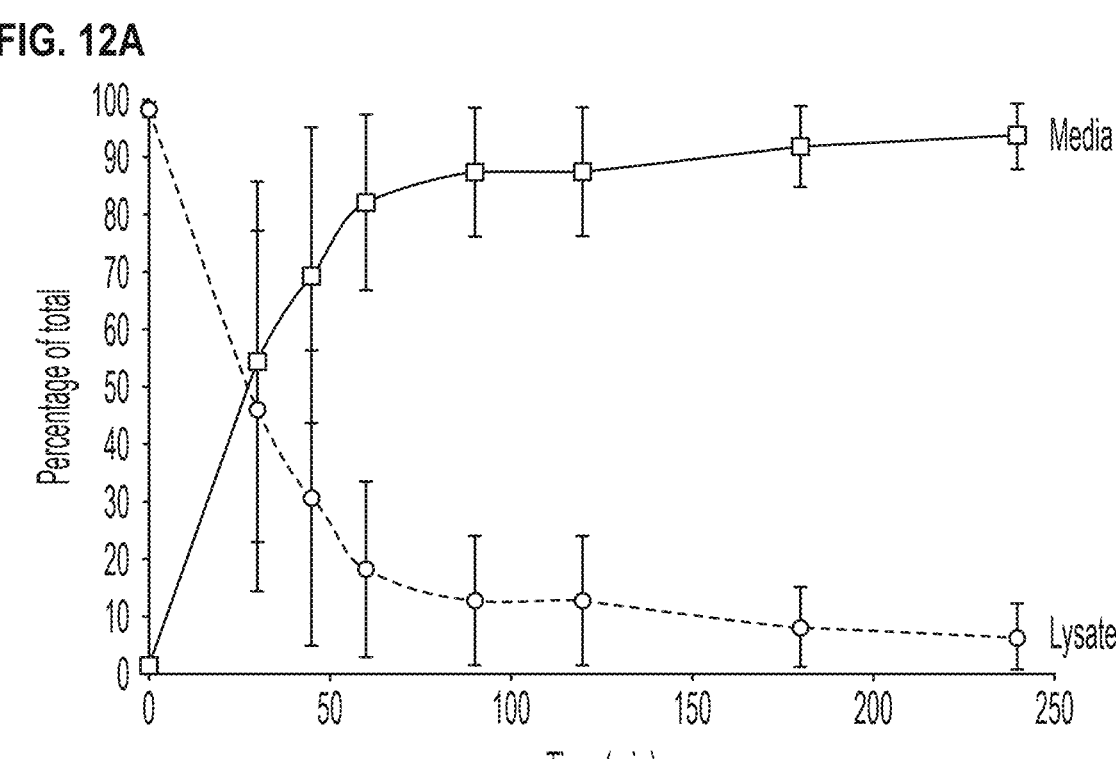
FIG. 12 is a set of graphs showing a pulse-chase experiment on the secretion of endogenous A1AT from Huh-7 cells (FIG. 12A); incorporation of $^{15}$N-labeled Arg and Lys in Huh-7 cells over time (FIG. 12B); MS/MS spectra of incorporation of $^{15}$N Arg (FIG. 12C); and MS/MS spectra of incorporation of $^{15}$N Lys (FIG. 12D).
FIG. 12C shows the peptide sequence ITPNLAEFAFSLYR (SEQ ID NO: 1)
FIG. 12D shows the peptide sequence SVLGQLGITK (SEQ ID NO: 2).

Pulse-chase experiments were carried out using radioactive $^{35}$S labeled cysteine and methionine to monitor A1AT maturation and secretion from Huh-7 cells using gel electrophoresis to monitor protein secretion (see FIG. 12A). The half-time of secretion was 30 minutes. These data assist in choosing appropriate chase time points for A1AT pcIC-FPOP. Therefore, pcIC-FPOP was performed on Huh-7 cells, a hepatocyte derived cellular carcinoma cell line that continually synthesizes A1AT, increasing the ability to detect protein modification by pcIC-FPOP coupled to mass spectrometry.

Figure 12B:
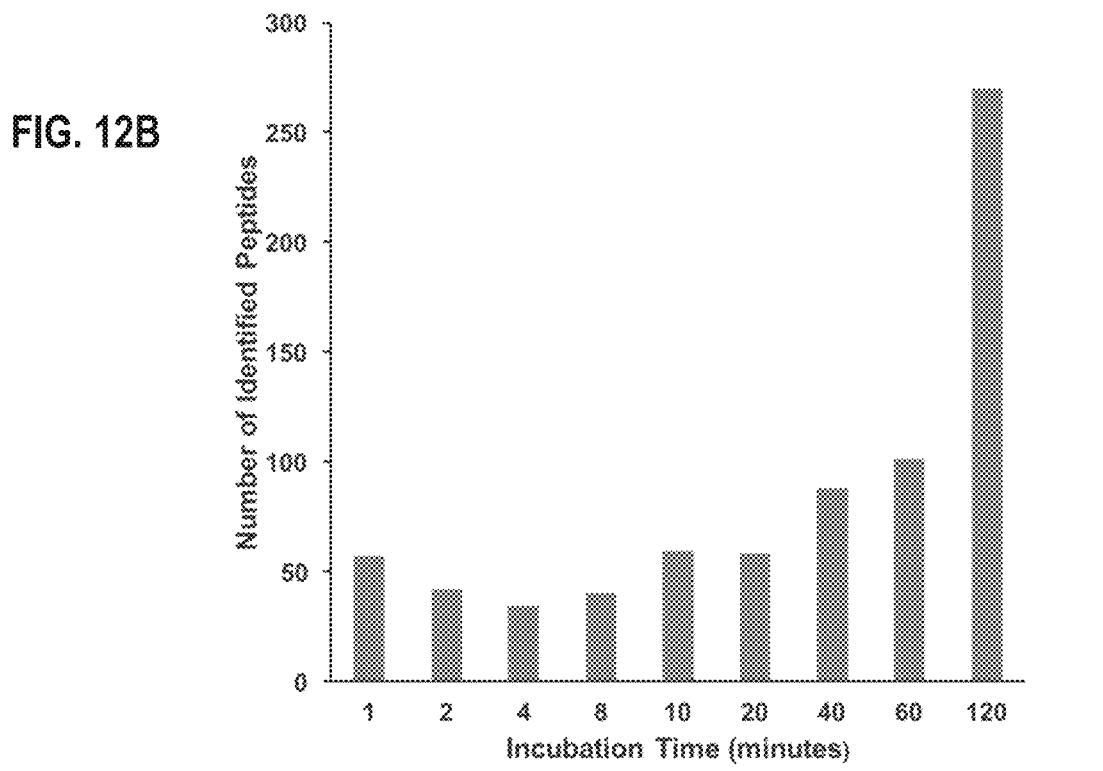
Figures 1, 12C:
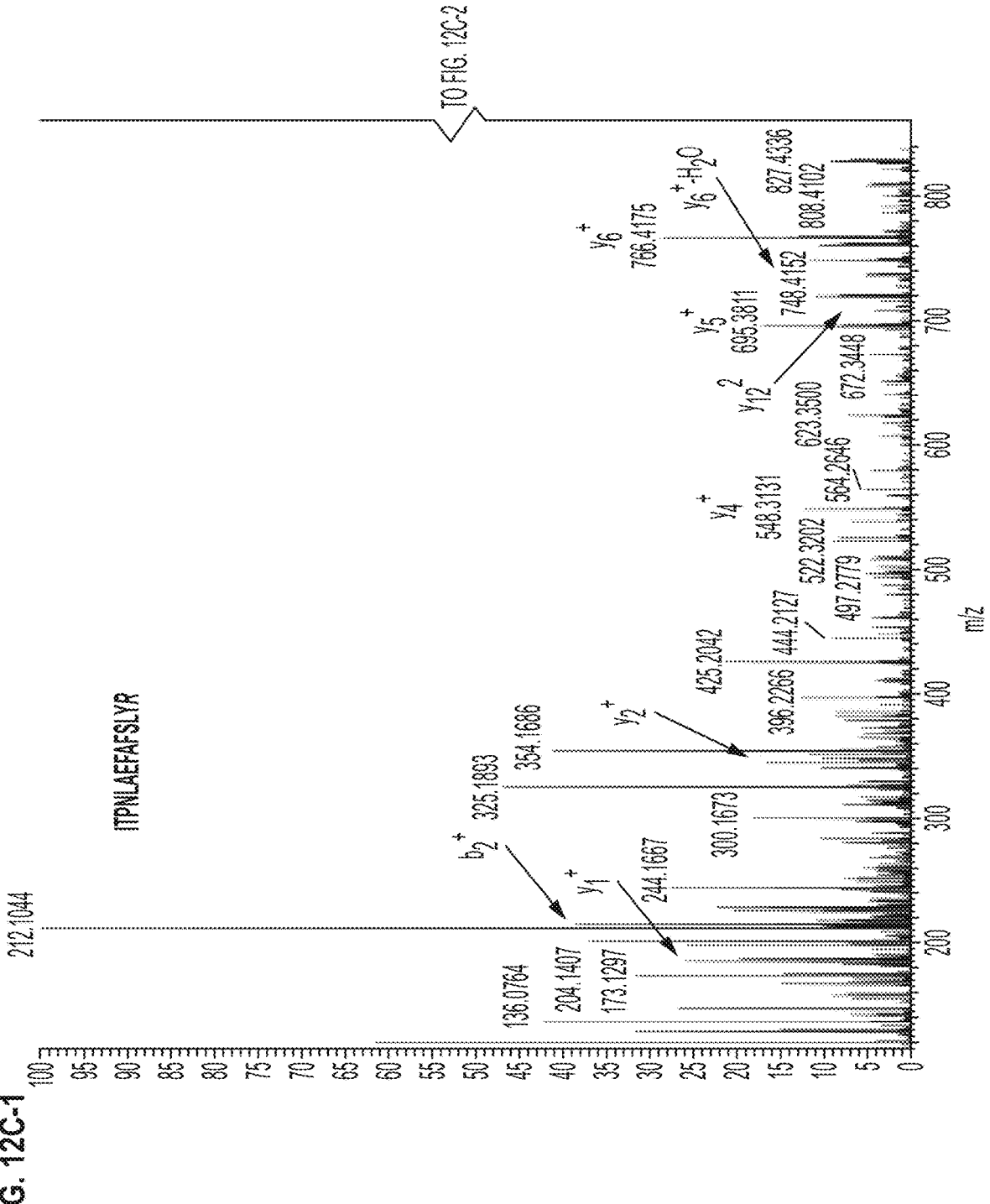
Figures 2, 12C:
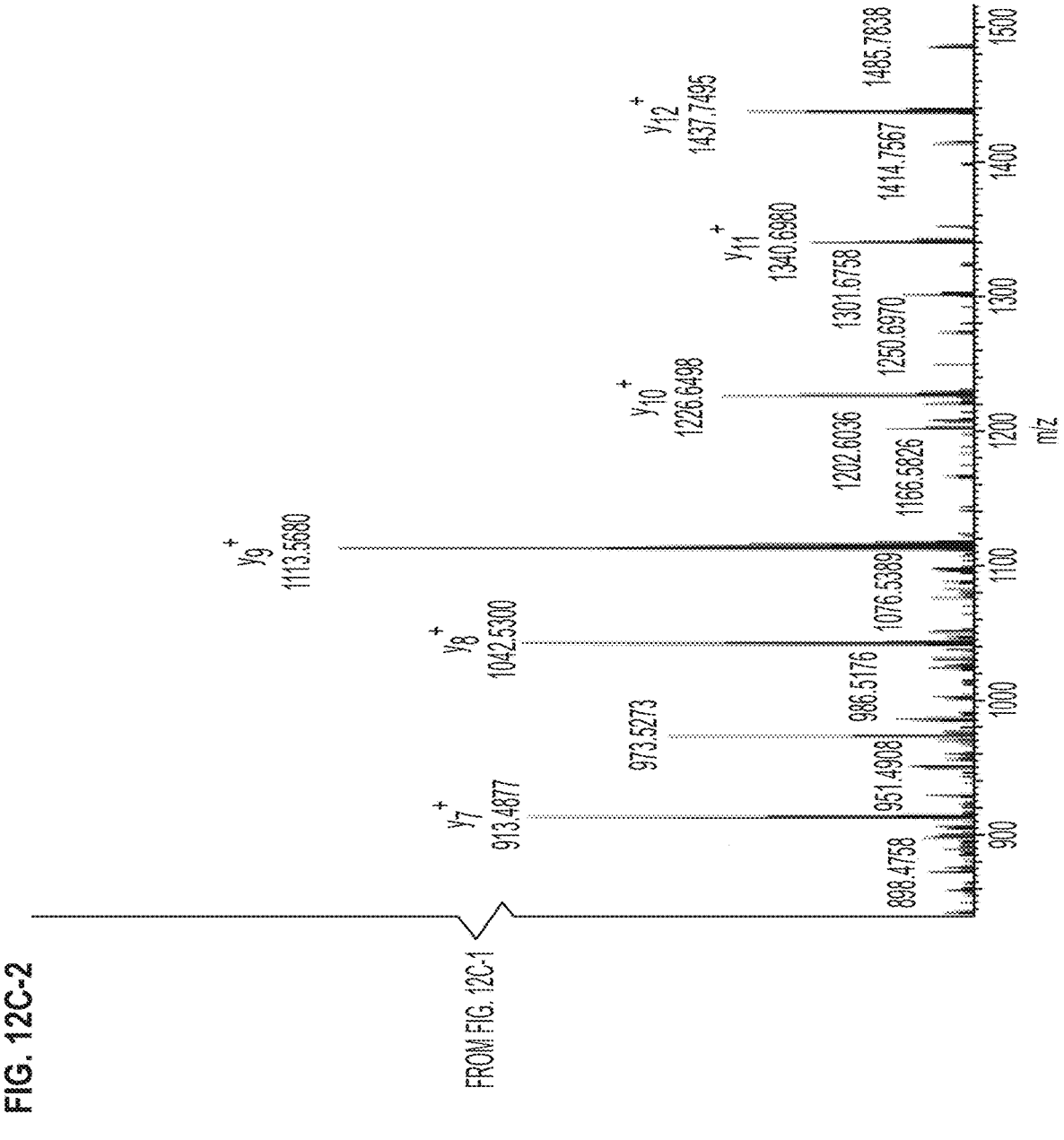
Figures 1, 12D:
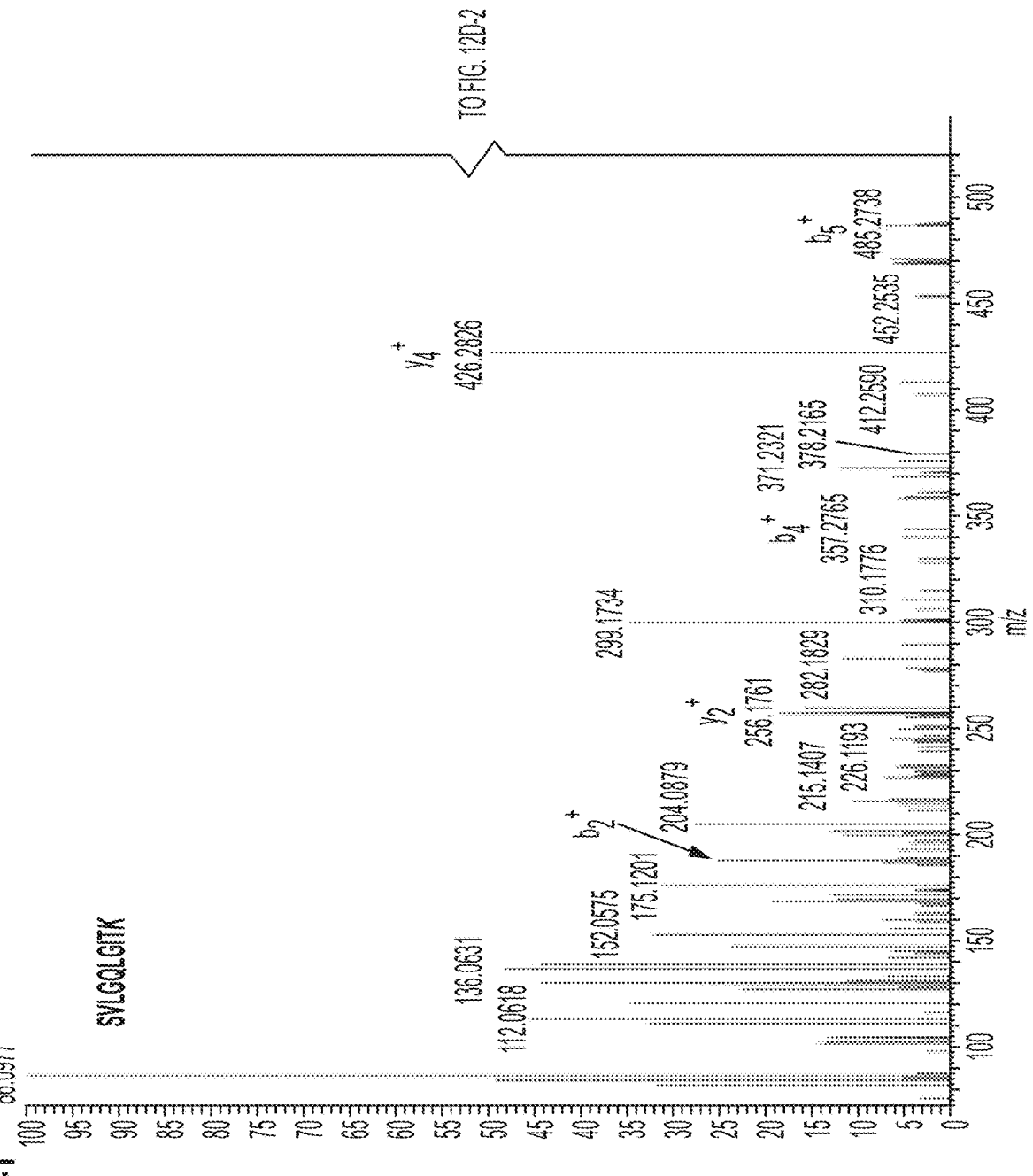
Figures 2, 12D:
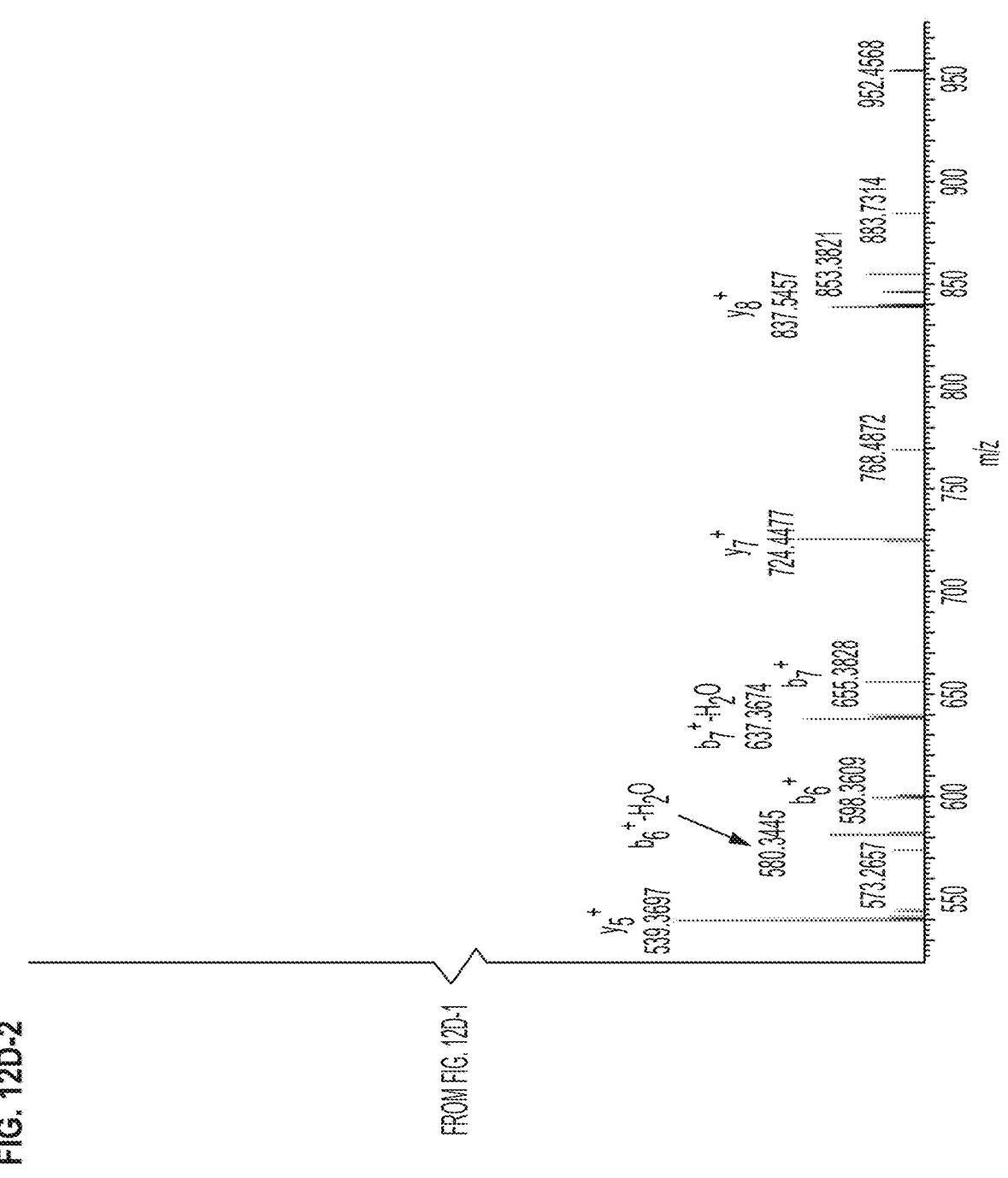

For these experiments, the $^{15}$N-labeled Arg and Lys SILAC reagents were used for the pulse step. Unlike traditional SILAC experiments where complete metabolic incorporation of the label is preferable, analyzing samples at short label incorporation times to detect newly synthesized proteins is more appropriate. To determine how long it takes for Huh-7 cells to incorporate the heavy labeled reagents, the cells were cultured in the presence of [15]N Arg and [15]N Lys for varying times. Mass spectrometry analysis of the cell lysates demonstrated that labeled peptides are observed following as little as 1 minute of incubation with increases at subsequent incubation times (see FIG. 12B). FIG. 12C and FIG. 12D shows MS/MS spectra of two heavy-labeled peptides in A1AT which are first detected in the 40 minute pulse, indicating that this protein can take up the label as it is being synthesized and that newly synthesized A1AT can be detected using this method. These data demonstrate the feasibility of using SILAC reagents for pcIC-FPOP.

Example 5. Study of Protein Interactions with Photoreactive Cross-Linking

In recent years, in vivo cross-linking has been used to map protein interactions in living cells. Photoreactive cross-linkers are especially suited for this study because their reaction is fast (microsecond to millisecond timescale) so they can capture short-lived intermediates. Photoreactive cross-linking requires the incorporation of photoreactive amino acid variants with diazirine chemistry for UV light-induced cross-linking. There variants can be introduced to the protein via cell culture medium similarly to the incorporation of $^{15}N$-labeled Arg and Lys for SILAC experiments. L-Photo methionine and leucine are commercially available for cross-linking in cells. To yield a high level of information on the interaction of chaperones during protein folding, performing cross-linking and pcIC-FPOP simultaneously is advantageous. In this manner, the interactions between chaperones and the protein are maintained while the oxidation data can identify the interaction sites at the amino acid residue-level.

Photoreactive cross-linkers L-Photo Met and L-Photo Leu require UV-A irradiation to initiate the cross-linking reaction. Suitable UV-A radiation preferably consists of wavelengths from 315-400 nm, however wavelengths between 350-365 also can be used for cross-linking. Huh-7 cells are cultured in the presence of L-Photo Met and L-Photo Leu for incorporation into newly synthesized A1AT. The protein then can be purified by immunoprecipitation and subjected to in vitro FPOP and to $H_2O_2$ incubation without laser irradiation as a control. Additional software which has been used to identify cross-links in vitro and in vivo, can be used to determine whether any cross-links have been formed. Then a 365 nm UV lamp can be used to induce cross-linking in the presence of $H_2O_2$ only and during FPOP with laser irradiation. Cross-linking in the absence of $H_2O_2$ and laser irradiation can be performed for comparison and control.

To perform pcIC-FPOP and photoreactive cross-linking together to study A1AT folding in cells, Huh-7 cells are cultured in RPMI 1640 medium. This medium lacks glucose and all amino acids. Prior to use, the medium is supplemented with glucose and all amino acids except Met, Leu, Arg, and Lys. The medium then is supplemented with L-Photo Met and L-Photo Leu and $^{15}N$-labeled Arg and Lys. The incorporation time of L-Photo Met and Leu can be tested to ensure the incubation time is sufficient for incorporation in A1AT. The pulse then is initiated by the addition of the supplemented medium to the cells. At various chase times, cells $H_2O_2$ is added to cells, and cells are subjected to excimer laser irradiation at 248 nm and UVA irradiation at 365 nm similar to the protocol described above.

Example 6. Mis-Folded Mutants of A1AT

More than 40 A1AT missense mutations, located throughout the structure, are associated with. mis-folding and symptoms of mild to severe A1AT deficiency. To test the ability of pcIC-FPOP to identify changes in the conformational distributions populated during folding, the in-cell folding of the two most common disease-associated mutations S (Glu264Val) and Z (Glu342Lys) which are associated with mild and severe secretion defects respectively) are studied. For Z, the mutation's severity is easily seen in the slow secretion from Huh-7 cells and the accumulation of a detergent insoluble aggregates in those cells (see FIG. 13). To broaden the sequence, structure and phenotypic coverage, the Siiyama (Ser53Phe) variant also is studied. This mutation occurs early in the sequence and is associated with severe disease. These three mutations are located throughout the A1AT structure and show strikingly different phenotypes in people and in *C. elegans*. These differences are supported by folding simulations which suggest different. mis-folded conformations for Z versus Siiyama. In contrast, to these two deleterious mutations, the S mutation is relatively benign, and people who are homozygous for S have circulating levels of A1AT that are approximately 40% of normal. In the folding, S folds similarly to wild-type A1AT but has a higher propensity to mis-fold reflecting this milder phenotype.

These three mutations in A1AT therefore allow testing of the sensitivity of pcIC-FPOP to changes in protein folding. The S mutant results in only mild defects and pcIC-FPOP results should be similar to those for wild-type except that there should be a higher. mis-folded population at longer chase times and likely more persistent interactions with components of the ER quality control machinery, e.g., molecular chaperones. In contrast, Z and Siiyama folding should significantly diverge from wild-type folding, and both are likely to alter interactions with the ER quality control machinery. While the Z mutation, Glu342Lys, is near the C-terminus of the 394-amino acid long mature A1AT, the Ser53Phe mutation in Siiyama is near the A1AT N-terminus. Thus, Siiyama could begin to mis-fold co-translationally and early in the chase. These three A1AT mutants thus provide a rigorous test of the ability of pcIC-FPOP to detect and molecularly characterize mild and severe. mis-folding and to determine how mutations alter interactions with molecular chaperones and other cellular components that target. mis-folded proteins.

Figure 13:
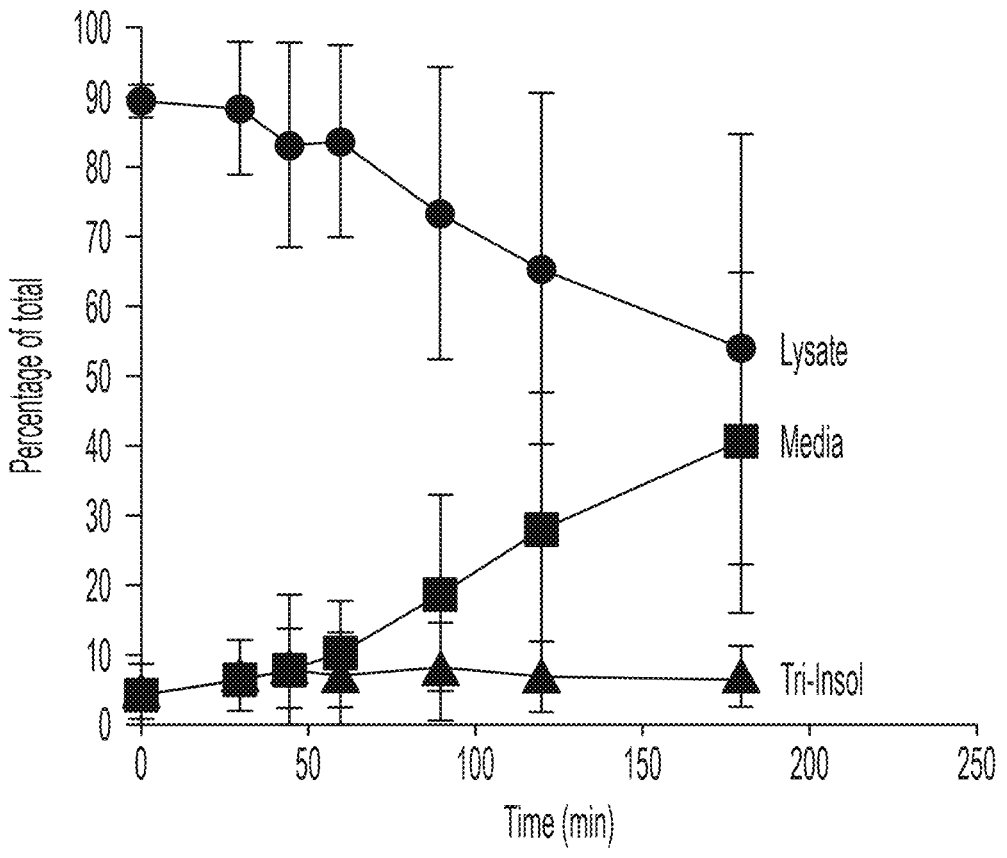
FIG. 13 is a graph showing results of a radioactive pulse-chase experiment for the Z mutant of A1AT in Huh-7 cells. Tri-insol indicates aggregated, detergent insoluble protein that is retained in cells.

Traditional pulse-chase experiments performed on the Z mutant demonstrate that this mutant secretes slower than the wild type protein further showing the effects of mis-folding on this protein (FIG. 13). These data help determine the best chase points to use to probe the folding pathway of this mutant.

Example 7. Optimizing Pulse and Chase Times for pcIC-FPOP

Similar to the testing described for wild type A1AT, both pulse and chase time points are optimized for each cell used. Since transient transfections generally are used to synthesize the proteins for study, the amount of time to generate a detectable population of labeled protein can vary. Therefore, the pulse time for each cell or mutant cell is tested and optimized. For example, since preliminary pulse-chase experiments show that the Z mutant of A1AT secretes more slowly than the wild type, different chase time points are used to study the folding of this mutant. It is likely that both the S and Siiyama mutants also require chase times that are different from Z and wild type. Traditional pulse-chase experiments on the different cells, such as the S and Siiyama mutants in Huh-7 cells to provide guidance on which chase times are optimal. Once pulse and chase times for each cell or mutant have been optimized, pcIC-FPOP can be used to study the folding pathway. LC-MS/MS analysis and data processing can be performed and the data compared to other pcIC-FPOP data.

REFERENCES

1. Ebbinghaus et al., Nat. Methods 7:319-323, 2010. Protein folding stability and dynamics imaged in a living cell.
2. Espino et al., Anal. Chem. 87:7971-7978, 2015. In Cell Footprinting Coupled with Mass Spectrometry for the Structural Analysis of Proteins in Live Cells. Electrospray ionization for mass spectrometry of large biomolecules.
3. Fenn, et al., Science 246:64-71, 1989.
4. Gau B C, Sharp J S, Rempel D L, and Gross M L, Anal Chem. 81(16): 6563-6571, 2009. Fast Photochemical Oxidation of Proteins Footprints Faster than Protein Unfolding.
5. Hambly D M, Gross M L. J. Am. Soc. Mass Spectrom. 16:2057-2063, 2005.
6. Hambly D, Gross M. Int. J. Mass Spectrom. 259:124-129, 2007.
7. Karas et al., Anal. Chem. 57:2935-2939, 1985. Influence of the wavelength in high-irradiance ultraviolet laser desorption mass spectrometry of organic molecules.
8. Nissley et al., Nat. Commun. 7:10341, 2016. Accurate prediction of cellular co-translational folding indicates proteins can switch from post- to co-translational folding.
9. Rinas et al., Anal Bioanal. Chem. 408:3021-3031, 2016. An efficient quantitation strategy for hydroxyl radical-mediated protein footprinting using Proteome Discoverer.
10. Rinas et al., Anal. Chem. 88(20):10052-10058, 2016. Development of a Microflow System for In-Cell Footprinting Coupled with Mass Spectrometry.
11. Smith et al., Curr. Opin. Struct. Biol. 30:7-16, 2015. NMR studies of protein folding and binding in cells and cell-like environments.
12. Zhang et al., Chem. Rev. 113:2343-2394, 2013. Protein analysis by shotgun/bottom-up proteomics.

What is claimed is:

1. A system comprising:
a plate with a plurality of open wells; an incubator comprising:
a frame defining a recess configured to receive the plate with the plurality of open wells and to removably accommodate the plate in the recess;
a removeable cover for the recess, wherein the cover is transparent to laser light of a first wavelength and wherein the cover encloses the recess so that a controlled environment is established in the recess for preserving function of cells cultured in the plurality of wells, wherein the controlled environment encompasses the plurality of open wells and a region of the recess defined between the plate and the frame;
an environmental supply coupled to the controlled environment and configured to supply heat and a gas mixture including carbon dioxide and water vapor to the controlled environment including the plurality of open wells and the region of the recess defined between the plate and the frame; and
for each well of the plurality of wells, a plurality of perfusion tubes disposed to dispense fluid to or from a distal end at a position of each well, wherein each perfusion tube of the plurality of perfusion tubes is configured at a proximal end to be connected in fluid communication with one of a plurality of corresponding reservoirs outside the incubator;
a laser source configured to emit a laser beam at the first wavelength;
the environmental supply comprising;
a thermal source configured to supply the heat to the controlled environment; and
a gas source configured to supply the gas mixture; the plurality of corresponding reservoirs;
a plurality of pumps in fluid communication with the plurality of corresponding reservoirs;
at least one processor; and
at least one memory including one or more sequences of instructions,
the at least one memory and the one or more sequences of instructions configured to, with the at least one processor, cause the at least one processor to control on or more components of a group of components comprising the laser, the thermal source, the gas source, and the plurality of pumps;
wherein the at least one memory and the one or more sequences of instructions are further configured to, with the at least one processor, cause the at least one processor to perform at least the steps of:
a. for a first time interval, operate at least one first pump of the plurality of pumps to perfuse each well with fluid from a first reservoir of the plurality of corresponding reservoirs;
b. for a second time interval after the first time interval operate at least one second pump of the plurality of pumps to perfuse each well with fluid from a different second reservoir of the plurality of corresponding reservoirs;
c. for a third time interval after the second time interval operate at least one third pump of the plurality of pumps to perfuse a first well of the plurality of wells with fluid from a different third reservoir of the plurality of corresponding reservoirs;
d. for a fourth time interval after the third time interval operate the laser source to illuminate the first well with the laser beam at the first wavelength;
e. after the fourth time interval operate at least one fourth pump of the plurality of pumps to perfuse the first well with fluid from a different fourth reservoir of the plurality of corresponding reservoirs.

2. The system as recited in claim 1, the at least one memory and the one or more sequences of instructions are further configured to, with the at least one processor, cause the at least one processor to repeat steps c, d and e for each remaining well of the plurality of wells.

3. The system as recited in claim 1, wherein
the first reservoir holds feeding media that includes at least one amino acid labeled with a mass spectrometry label;
the second reservoir holds feeding media that does not include the mass spectrometry label;
the third reservoir holds hydrogen peroxide; and
the fourth reservoir holds a quench solution.

4. The system as recited in claim 1, further comprising:
the plurality of perfusion tubes including four perfusion tubes connected at the distal end to each open well;
wherein a first perfusion tube of the four perfusion tubes of each open well is connected between each open well and the first reservoir;

wherein a second perfusion tube of the four perfusion tubes of each open well is connected between each open well and the different second reservoir;

wherein a third perfusion tube of the four perfusion tubes of each open well is connected between each open well and the different third reservoir;

wherein a fourth perfusion tube of the four perfusion tubes of each open well is connected between each open well and the different fourth reservoir.

5. The system as recited in claim 4, wherein the proximal end of each perfusion tube of the four perfusion tubes reaches outside the frame of the incubator to be in fluid communication with one of the plurality of pumps to move fluid to or from one of the plurality of corresponding reservoirs into each well.

6. The system as recited in claim 4, wherein the four perfusion tubes pass through openings defined by the frame of the incubator.

7. The system as recited in claim 1, wherein a mass of the incubator is less than 500 grams.

8. The system as recited in claim 1, wherein a maximum size dimension of the incubator is less than 150 millimeters.

9. The system as recited in claim 1, wherein the first wavelength is about 248 nanometers and the cover comprises fused quartz silica.

10. The system as recited in claim 1, wherein the thermal source is connected with the at least one processor by a communication line or a power line or both.

11. The system as recited in claim 1, wherein the gas source is connected with the at least one processor by a communication line or a power line or both.

* * * * *